United States Patent
Viovy et al.

(10) Patent No.: US 10,704,074 B2
(45) Date of Patent: Jul. 7, 2020

(54) METHOD FOR DETECTING ORGANISMS IN A DILUTED SAMPLE

(71) Applicants: Jean-Louis Viovy, Paris (FR); Stephanie Descroix, Paris (FR); Laurent Malaquin, Aiguesvives (FR); Iago Pereiro, Paris (FR); Lucile Alexandre, Saint Martin Bellevue (FR)

(72) Inventors: Jean-Louis Viovy, Paris (FR); Stephanie Descroix, Paris (FR); Laurent Malaquin, Aiguesvives (FR); Iago Pereiro, Paris (FR); Lucile Alexandre, Saint Martin Bellevue (FR)

( * ) Notice: Subject to any disclaimer, the term of this patent is extended or adjusted under 35 U.S.C. 154(b) by 0 days.

(21) Appl. No.: 15/520,922

(22) PCT Filed: Oct. 23, 2015

(86) PCT No.: PCT/EP2015/074654
§ 371 (c)(1),
(2) Date: Apr. 21, 2017

(87) PCT Pub. No.: WO2016/062878
PCT Pub. Date: Apr. 28, 2016

(65) Prior Publication Data
US 2017/0335364 A1 Nov. 23, 2017

(30) Foreign Application Priority Data
Oct. 24, 2014 (FR) ...................................... 14 60246

(51) Int. Cl.
| | |
|---|---|
| *C12Q 1/04* | (2006.01) |
| *G01N 33/543* | (2006.01) |
| *G01N 33/569* | (2006.01) |
| *C12M 1/34* | (2006.01) |
| *C12M 1/00* | (2006.01) |
| *G01N 33/487* | (2006.01) |
| *B05D 1/00* | (2006.01) |
| *C12M 1/12* | (2006.01) |

(52) U.S. Cl.
CPC ............. *C12Q 1/04* (2013.01); *C12M 41/36* (2013.01); *C12M 47/02* (2013.01); *G01N 33/487* (2013.01); *G01N 33/54313* (2013.01); *G01N 33/54326* (2013.01); *G01N 33/569* (2013.01); *B05D 1/00* (2013.01); *C12M 1/00* (2013.01); *C12M 25/00* (2013.01); *C12Q 2304/80* (2013.01)

(58) Field of Classification Search
CPC .............................................. G01N 33/54313
See application file for complete search history.

(56) References Cited

FOREIGN PATENT DOCUMENTS

| | | | | |
|---|---|---|---|---|
| WO | 2006066216 A2 | 6/2006 | | |
| WO | WO 2006/066216 | * | 6/2006 | ............. G01N 33/05 |
| WO | WO 2009/008925 | * | 1/2009 | ............. C12M 3/00 |
| WO | 2013121216 A1 | 8/2013 | | |
| WO | 2013126774 A2 | 8/2013 | | |
| WO | 2013165615 A2 | 11/2013 | | |
| WO | 2014037674 A1 | 3/2014 | | |

OTHER PUBLICATIONS

Tae Seok Seo, "Highly integrated microdevice for ultrasensitive pathogen detection," Proceedings of the 2010 5th IEEE International Conference on Nano/Micro Engineered and Molecular Systems (NEMS), Jan. 20-23 Xiamen, China, pp. 1065-1068.
Beyor et al., "Integrated Capture, Concentration, Polymerase Chain Reaction, and Capillary Electrophoretic Analysis of Pathogens on a Chip," Anal. Chem. 2009, 81, 3523-3528.
International Search Report for International Application PCT/EP2015/074654 dated Dec. 17, 2015, seven pages.
Malvern Instruments Wordwide, "A basic guide to particle characterization." (2015).
Hung, PJ, Lee, PJ, Sabounchi, P., Lin, R.,and Lee, LP; "Continuous Perfusion Microfluidic Cell Culture Array for High-Throughput Cell-Bases Assays," Biotechnology and Bioengineering, 89(1): 1-8 (Jan. 5, 2005).
Sivagnanam, V, Song, B., Vandevyver, C., Bunzli, JCG, Gijs, MAM; "Selective Breast Cancer Cell Capture, Culture and Immunocytochemical Analysis Using Self-Assembled Magnetic Bead Patterns in a Microfluidic Chip," Langmuir, 26(9): 6091-96 (2010).
CIPO Office Action for Application CN20158061309 dated Jun. 3, 2019.
EP3210022 International Search Report (dated Apr. 28, 2016).
EP3210022 Written Opinion (dated Dec. 16, 2015).
EP3210022 International Preliminary Report on Patentability (dated May 9, 2017).

* cited by examiner

*Primary Examiner* — Bin Shen
(74) *Attorney, Agent, or Firm* — Klintworth & Rozenblat IP LLP

(57) ABSTRACT

The invention relates to a method for detecting organisms in a liquid sample, comprising the provision of a capture area including particles in a liquid medium and subjected to a hydrodynamic flow, wherein the organisms to be detected are capable of binding to these particles, the method comprising the steps of:
(a) circulating the sample through the capture area;
(b) circulating a growth medium through the capture area; and
(c) determining the presence, nature or concentration of organisms in the capture area;
said particles being retained in the capture area as a fluidized bed for at least one part of these steps.
The invention also relates to a system for implementing this method.

18 Claims, 4 Drawing Sheets

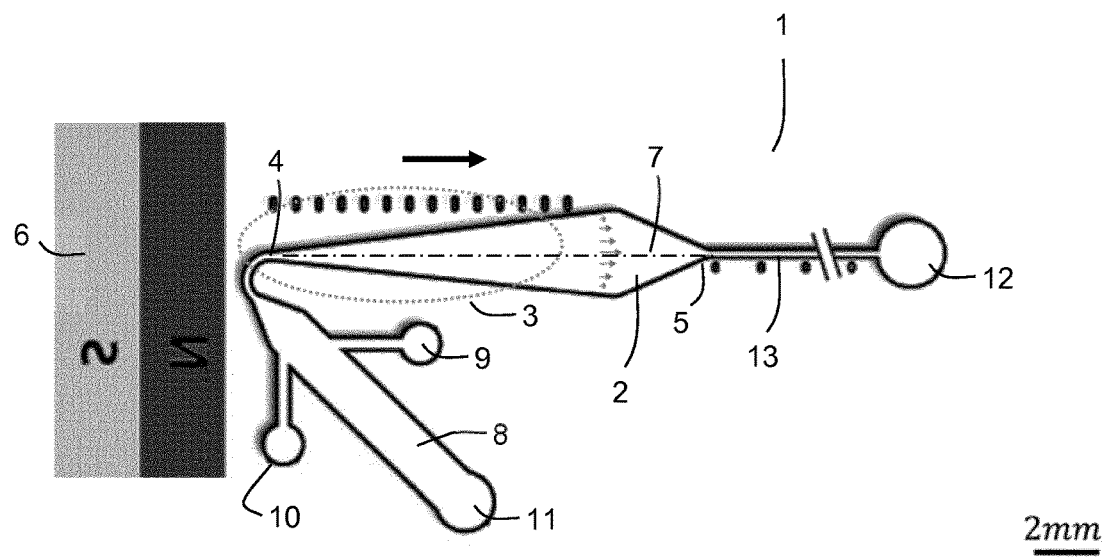
Fig. 1
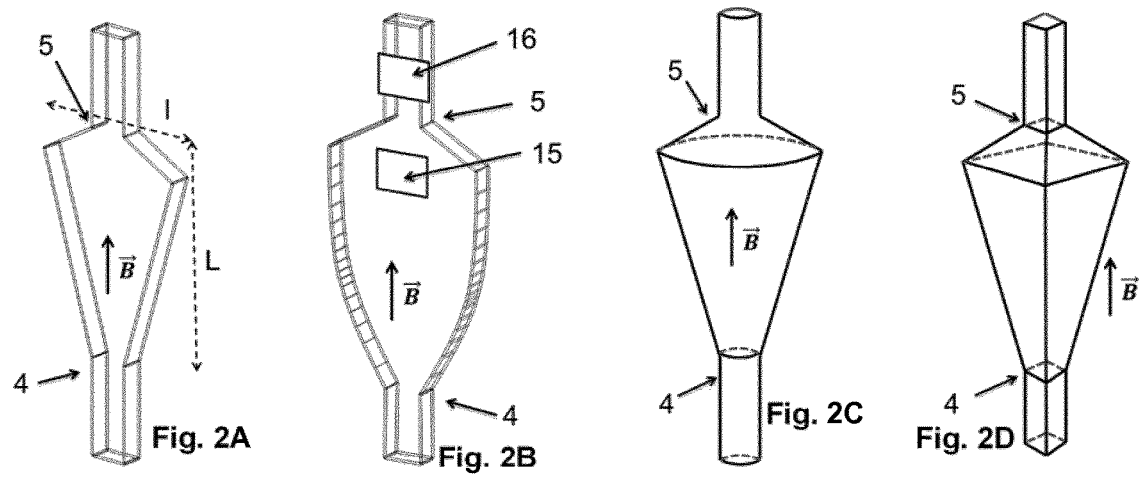
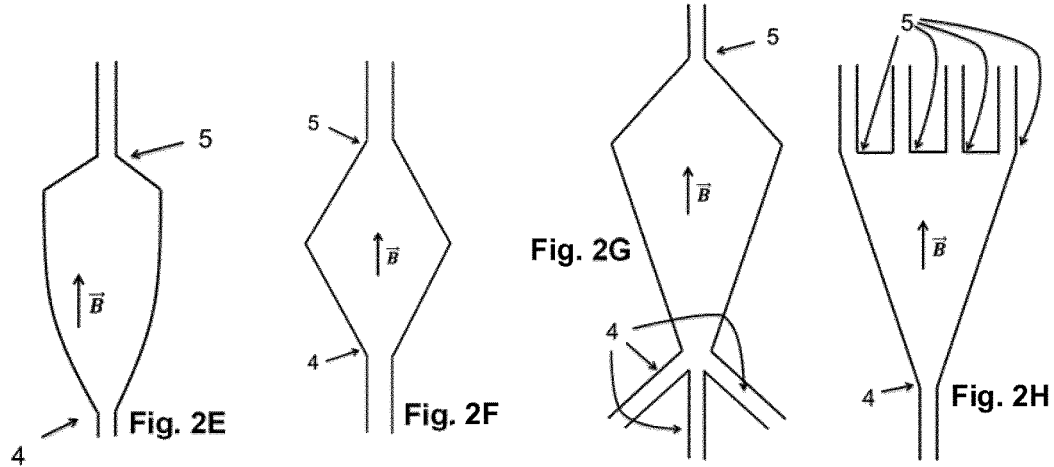

METHOD FOR DETECTING ORGANISMS IN A DILUTED SAMPLE

CROSS-REFERENCE TO RELATED APPLICATIONS

The present application is the U.S. National Stage of International Patent Application No. PCT/EP2015/074654, filed Oct. 23, 2015, which claims benefit of priority under 35 U.S.C. 119 to French patent application number 1460246, filed Oct. 24, 2014, and entitled "METHOD FOR DETECTING ORGANISMS IN A DILUTED SAMPLE," the contents of which are herein incorporated by reference in their entirety.

FIELD OF THE INVENTION

The present invention relates to a method for detecting organisms in a diluted sample. It also relates to a method for preparing organisms from a diluted sample. It further relates to fluidic systems adapted for implementing these methods.

TECHNICAL BACKGROUND

The detection, the characterization, the identification of biological species and in particular of organisms such as bacteria is a need which relates to many fields, for example medical or veterinary diagnostic, food safety or the environment. This is also a need in various fields of production, in biotechnology and pharmaceuticals. Finally, this is a need in many fields of research in life sciences and in pharmacy.

A particularly important example is that of bacteria. If some are used in industry for the production of foodstuffs, of chemical products or drugs, but also for the treatment of wastewaters, others may prove to be dangerous for health. In many cases, a rapid detection and of identification of these bacteria is therefore critical. Moreover, it is often not sufficient to detect traces of bacteria, but it is also often also necessary to be aware of their condition (live or dead), their infectivity and their resistance to such or such an antibiotic.

Therefore, it is desirable to know how to detect bacteria in a sample possibly containing a large variety of microorganisms. The response time has to be as short as possible, the confidence as high as possible, and the handling operations to be carried out as simple as possible.

Presently, the standard system for identifying bacteria involves the culture of colonies on a more or less selective medium depending on cases, and manual counting, or analysis of the content of the colonies after culture, for example, by molecular analysis technologies like mass spectrometry. It is then necessary to wait for approximately 24 to 48 hours for the development of the bacteria. Further, the required facilities, as well as the personnel, have to be specialized, even if computer programming tools may be useful. In order to identify bacteria strains, a morphological comparison, tests of resistance to antibiotics, or an identification by a colorimetric method, or a combination of such characterizations should further be carried out. This method is therefore inexpensive, quite reliable and easy to implement, but it requires an important concentration of bacteria, as well as a very significant operation time.

In document CN 102094062, a method was proposed in which the sample is passed through a filter, so that the bacteria accumulate in the filter; these bacteria are then cultured by placing the filter in a culture medium, and the metabolites from the growth of the bacteria are detected. This method is complex and requires a long analysis time.

It is also known how to culture cells in a system based on fluidized beds. For example, in document CN 201933088 a system was proposed for the culture of mammal cells adherent on a solid substrate, comprising a fluidized bed comprised between two porous plates, and perfused by a gas for promoting the culture. This system is, however, not suitable for diagnostic or detection applications on samples of a small volume.

In document CN 1303924, a method was proposed for producing viruses inside animal cells, themselves adherent to particles maintained within a magnetically stabilized fluidized bed. The method provides oxygenation, exchange of culture medium, and the collection of viruses at the outlet of the chamber. This method is adapted for production; it requires the preliminary injection of a large number of cells and therefore does not allow the detection of rare cells.

In document WO 86/05202 still another cell culture system was proposed on a fluidized bed, for the culture of tissues or fermentation, involving the treatment of a portion of the treated fluid in the fluidized bed in an ancillary chamber, and its reinjection into the bed. This system further requires a large initial number of cells, and is therefore not adapted to the detection of rare cells.

Other studies focused on more direct and sensitive detection methods, in microfluidic devices.

For example, in the article *Soft Inertial Microfluidics for High Throughput Separation of Bacteria from Human Blood Cells*, in Lab Chip, 9:1193-1199 (2009), a continuous separation of cells by a physical method, by using the relationship between the inertia of the objects to be sorted and their characteristic dimensions, was described. This method makes it possible to work at a high flow rate, but the separation remains inaccurate in terms of resolution size. Moreover, many bacteria or different cells may have the same size, and this sorting criterion is therefore insufficient.

Electrophoretic sorting methods may also be used. Indeed, the electrophoretic mobility of a bacterium depends on the charge and on the radius of the bacterium. Electrophoresis thus makes it possible to concentrate the sought bacteria, but also to discard the dead bacteria, by modifying the electric direction of the applied field over very short times, as described in the article *Enrichment of viable bacteria in a micro-volume by Free-flow electrophoresis*, in Lab Chip, 12: 451-457(2012). Alternatively, the dielectrophoresis force which is based on the difference of dielectric constants of the objects to be sorted out, may be used.

Such methods have to be coupled with PCR (polymerization chain reaction) systems or with other genomic analyses in order to identify the bacteria which are present, as discussed in the article *A microfluidic chip integrating DNA extraction and real-time PCR for the detection of bacteria in saliva*, in Lab Chip, 13: 1325-1332 (2013). However, specificity and sensitivity often remain insufficient.

Still another method is the capture by binding between antibody and antigen. Mention may notably be made of a use of this method for capturing bacteria by directly grafting antibodies on the microfluidic channels of a circuit, in the article *On-chip microfluidic biosensor for bacterial detection and identification*, in Sensors and Actuators B, 126: 508-514 (2007). In this case, the grafting of the antibodies is carried out by silanization and it is necessary to let the bacteria settle so that the capture is efficient. The flow rate is insufficient when it is required to detect a few bacteria in large volume samples, as is the case for example for diagnostic analyses and food safety analyses.

In the article *Immunomagnetic bead-based cell concentration microdevice for dilute pathogen detection*, in Biomed Microdevices, 10:909-917 (2008), a microfluidic system is described wherein magnetic beads bearing antibodies are immobilized by a side magnet, in order to capture bacteria. However, the capture efficiency is only of 2 CFU per μL, which is very insufficient for the required efficiency levels, for example in diagnostic or food analysis applications.

In document WO 2014/037674 a microfluidic fluidized bed is described, with a circulation of magnetic beads controlled by an external magnetic field, notably for the capture of bacteria, still by grafting specific antibodies on the magnetic beads. However, this system does not have sufficient sensitivity for detecting a few bacteria in large volumes of samples. Moreover, it does not make it possible to differentiate live bacteria from dead bacteria.

There are also cell types which are particularly interesting to characterize, to concentrate, to culture and/or to amplify: for example, these are yeasts, or superior eukaryotic cells, notably mammal cells and particularly human cells. For example, biotechnology and medicine, notably regenerative medicine or graft medicine, are interested in novel methods for characterization, for sorting and for developing stem cells, progenitor cells, pluripotent or totipotent cells. For example, in the article *Microfluidic Capture of Endothelial Colony-Forming Cells from Human Adult Peripheral Blood: Phenotypic and Functional Validation In Vivo*, in Tissue Engineering Part C, vol. 21: 274-283 (2015), doi: 10.1089/ten.tec.2014.0323, Lin et al. describe a method allowing the microfluidic capture of human cells, endothelial colony forming cells (ECFC). However, in this method, microfluidics is only used for capture, and it is then necessary to transfer the cells of interest into conventional culture plates, which leads to a method which is long and expensive in handling operation time.

Therefore, there is an actual need for developing systems for detecting rare bacteria in quite significant volumes of samples, in an easy, automated and rapid manner, and for identifying their infectivity or their proliferation potential. Similar problems also exist for other unicellular or pluricellular organisms, like yeasts or parasites, or eukaryotic cells, for example stem cell or cancer cells.

SUMMARY OF THE INVENTION

The present invention makes it possible to overcome the drawbacks of the state of the art. It notably provides a method for detecting organisms (such as bacteria) in a liquid sample by capturing even a very small number of organisms on particles retained in a capture area, and then multiplying or growing these organisms in situ in the capture area, and finally detecting the thereby multiplied organisms.

The use of a fluidized bed of particles in the method makes it possible to use relatively significant fluid flow rates, and to optimize the interactions between the different species at stake in the capture area (and notably between the particles and the organisms which are capable of binding to them).

Thus, the invention relates to the following objects.

Object 1. A method for detecting organisms in a liquid sample, comprising providing a capture area including particles in a liquid medium and subject to a hydrodynamic flow, wherein the organisms to be detected are capable of binding to these particles, wherein the method comprises the steps of:
(a) circulating the sample through the capture area;
(b) circulating a growth medium through the capture area; and
(c) determining the presence, nature or concentration of the organisms in the capture area;
said particles being retained in the capture area in the form of a fluidized bed during at least part of these steps.

The term "organism" in the present application refers to any microorganism or any unicellular or pluricellular organism which may grow in a suitable medium, called herein a "growth medium".

The term also applies to organisms in a quiescent form, for example spores, shells, etc. The term also encompasses individual cells or cell aggregates from more complex organisms, like for example mammal cells, either natural or mutated.

The term "fluidized bed" in the present application refers to a state in which the particles suspended in a flowing liquid medium behave like a fluid, i.e. they are in motion relative to each another, and may adapt their mutual configuration to the shape of the chamber in which they are contained, but they are not globally driven by said fluid, as will be discussed in more detail below.

The term "fluidized bed" is defined as opposed to a non-fluidized bed, also called a "compact bed", but also as opposed to a simple suspension, in which the particles are globally driven at the velocity of the fluid.

The invention thus provides a growth (e.g. multiplication) of the target organisms during step (b) of culturing the organisms in situ in the capture area. Thus, detection is facilitated, and sensitivity is increased.

On the other hand, the invention makes it possible to differentiate live organisms from dead organisms; or to differentiate organisms capable of proliferating from organisms not capable of proliferating or developing; or to differentiate organisms capable of proliferating and of developing more or less rapidly.

Thus, the invention makes it possible to obtain information on the metabolism, the proliferation capability or other properties of some organisms in some environments.

Object 2. The method according to claim 1, wherein the growth medium comprises nutrients for the organisms.

Object 3. The method according to one of objects 1 to 2, wherein the particles are retained in the capture area as a fluidized bed during part, and preferably during the totality of step (a).

Object 4. The method according to one of objects 1 to 3, wherein the particles are retained in the capture area as a fluidized bed during part, and preferably during the totality, of step (b).

Object 5. The method according to one of objects 1 to 4, wherein the particles are retained in the capture area as a fluidized bed during part, and preferably during the totality of step (c).

Object 6. The method according to one of objects 1 to 5, wherein the particles are retained in the capture area as a compact bed during part, preferably during the totality of step (c).

Object 7. The method according to one of objects 1 to 6, wherein the velocity of the hydrodynamic flow decreases in the capture area, in the direction of the hydrodynamic flow.

Object 8. The method according to one of objects 1 to 7, wherein the retention of the particles in the capture area is obtained by applying a force opposed to the hydrodynamic flow.

Object 9. The method according to object 8, wherein the force opposes to the hydrodynamic flow decreases in the capture area, in the direction of the hydrodynamic flow.

Object 10. The method according to one of objects 8 to 9, wherein the force opposed to the hydrodynamic flow is essentially aligned with the direction of the hydrodynamic flow.

Object 11. The method according to one of objects 8 to 10, wherein the force opposed to the hydrodynamic flow is a magnetic force, the particles being magnetic particles, preferably super-paramagnetic particles.

Object 12. The method according to one of objects 8 to 10, wherein the force opposed to the hydrodynamic flow is an electrostatic force, the particles being charged particles.

Object 13. The method according to one of objects 8 to 10, wherein the force opposed to the hydrodynamic flow is a gravitational or centrifugal force, the particles having a density different from that of a surrounding liquid.

Object 14. The method according to one of objects 1 to 13, wherein the organisms to be detected are capable of binding to the particles via ligands, preferably antibodies.

Object 15. The method according to one of objects 1 to 14, wherein the particles have an average size Dv50 from 1 nm to 500 µm, preferably from 50 nm to 100 µm, and more particularly from 1 µm to 50 µm.

Object 16. The method according to one of objects 1 to 15, wherein the organisms are selected from prokaryotic cells, bacteria, yeasts, unicellular or pluricellular parasites, fungal cells, eukaryotic cells and notably mammal cells or plant cells, or functional assemblies of such cells; according to some preferred embodiments, said organisms are selected from pathogen organisms, stem cells, genetically modified organisms, and cancer cells.

Object 16a. The method according to one of objects 1 to 15, wherein the organisms are selected from endothelial cells, hematopoietic cells, epithelial cells, fetal cells, pluripotent cells, totipotent cells, and induced pluripotent stem cells.

Object 17. The method according to one of objects 1 to 16a, wherein step (c) is carried out by measuring a property in the capture area.

Object 17a. The method according to one of objects 1 to 16a, wherein the step (c) is performed by measuring a property outside the capture area.

Object 18. The method according to object 17 or 17a, wherein step (c) is carried out during step (b), in a one-time or repeated manner over time.

Object 18a. The method according to one of objects 1 to 18, wherein step (c) is carried out by the detection, the culture or the identification of organisms or of species transported out of the capture area by a hydrodynamic flow during step (b).

Object 19. The method according to object 17 or 17a, wherein step (c) is carried out after step (b).

Object 20. The method according to one of objects 1 to 16a, comprising:
transferring species out of the capture area after step (b), step (c) being carried out by measuring a property on the transferred species; the species preferably being species secreted by the organisms possibly bound to the particles in the capture area, or constituents of these organisms, if necessary released by a lysis.

Object 20a. The method according to one of objects 1 to 16a or 20, comprising:
sampling particles out of the capture area after step (b), step (c) being carried out by measuring a property on the sampled particles.

Object 20b. The method according to one of objects 1 to 19, further comprising:
transferring species out of the capture area after step (b) or during step (b).

Object 20c. The method according to object 20b, wherein step (c) is carried out by measuring a property on the transferred species.

Object 20d. The method according to object 20c, wherein the species are secreted by organisms bound to particles in the capture area, or constituents of these organisms, optionally released by a lysis.

Object 20e. The method according to object 20c, wherein the species are organisms bound to the particles in the capture area, or organisms derived from such organisms.

Object 20f. The method according to one of objects 17 to 20e, wherein the measured property is a biological or biochemical property, such as an affinity, a proliferation capability, a phenotype or a phenotypic property, a genotype or a genetic characteristic, a mutation, an expression level, a morphology or a capability of proliferation.

More generally, by "measured property" is meant any characteristic which makes it possible to differentiate a molecule from other molecules, a molecular assembly from other molecular assemblies, or a cell from other cells, or a cell type from other cell types, or a condition of a cell from other conditions of a cell, an organism from other organisms.

Object 21. The method according to one of objects 17 to 20f, wherein the measured property is a force, a displacement, a pressure, a flow rate, a mass, a density, a porosity, a viscosity, an elasticity, a viscoelasticity, an optical density, a turbidity, a texture property, an intensity measurement or a radiation absorption coefficient.

Object 22. The method according to one of objects 17 to 20f, wherein the measured property is the volume occupied by the particles in the capture area or a size of this occupied volume, optionally when the particles are in the form of a compact bed.

The expression "volume occupied by the particles" is generally meant as referring to the volume of the capture area in which the particles (and preferably the organisms) are situated, or the volume of the bed of particles.

Object 23. The method according to object 22, wherein the concentration of organisms in the sample is determined as a function of the time required during step (b) for the volume occupied by the particles in the capture area to reach a threshold value.

Object 24. The method according to one of objects 1 to 23, wherein step (c) includes a biological or biochemical analysis, preferably a genetic analysis, a proteomic analysis, a toxin analysis, or a measurement of metabolic activity, and more particularly, preferably by amplification and/or hybridization of nucleic acid, sequencing nucleic acid, immunoagglutination or immunoadsorption assay by a bound enzyme.

Object 25. The method according to one of objects 1 to 24, wherein step (b) makes it possible to increase the number of organisms in the capture area by a factor of at least 10, preferably at least 100, or even at least 1,000 or at least 10,000 or at least 100,000, based on the number of organisms present in the capture area at the end of step (a).

Object 26. The method according to one of objects 1 to 25, which is implemented in a microfluidic system.

Object 27. The method according to one of objects 1 to 26, comprising a molecular amplification before step (c) or during step (c).

Object 28. The method according to one of objects 1 to 27, further comprising circulating a medium comprising a target agent for the organisms through the capture area, preferably either after the step of circulating the growth medium or during this step, the target agent being more particularly preferably incorporated to the growth medium.

Object 29. The method according to object 28, for screening drugs or biocides, wherein the target agent is a potential drug or biocide.

Object 30. The method according to one of objects 1 to 29, wherein the sample is derived from the environment, or from a food product, or from a bodily fluid.

"Environment" is meant in its broadest sense i.e. any type of solid, gas or liquid support, and any type of application, such as for example and in a non-limiting way, air, water, soils, buildings, human installations, clothes, surfaces, plants, utensils, waste, or elements related to security, forensic analyses.

Similarly, "bodily fluid" is meant in its broadest sense, for example comprising blood or treated blood, plasma, serum, tears, milk, saliva, sweat, samples stemming from the sampling with swabs on all body parts, urine, feces, or fluid samples obtained by any types of pre-samplings from body parts, such as for example biopsies or operating parts. Bodily fluids may be from human bodies. Alternatively, they may be from any types of animal or plant species.

Also, the notion of "food products" is meant in its broadest sense, whether these are from human or animal food, but also from any raw material, transformed product, intermediate product, effluent, involved in nutrition or food production.

The method of the invention may notably be applied by means of the fluidic system of the following objects.

Object 31. A fluidic system for detecting organisms in a liquid sample, comprising:
    at least one chamber including at least a fluid inlet and a fluid outlet and including a capture area;
    means for circulating the liquid sample through the capture area;
    means for circulating a growth medium through the capture area;
    means for applying a force field in the capture area, said force field being configured for retaining particles in the capture area in the form of a fluidized bed when the capture area is subjected to a hydrodynamic flow, wherein the organisms to be detected are capable of binding to the particles;
    means for determining the presence, nature or concentration of the organisms in the capture area.

Object 31a. The fluidic system according to object 31, comprising at least one additional chamber or tank, in fluid connection with an outlet of the chamber.

Object 31b. The fluidic system according to one of objects 31 to 31a, further comprising a device for regulating the temperature of the chamber.

Object 32. The fluidic system according to one of objects 31 to 31b, which is a microfluidic system.

Object 33. The fluidic system according to one of objects 31 to 32, wherein the force field is essentially aligned with the direction of the hydrodynamic flow in the capture area.

Object 34. The fluidic system according to one of objects 31 to 33, wherein the force field has a decreasing intensity in the direction of the hydrodynamic flow in the capture area.

Object 35. The fluidic system according to one of objects 31 to 34, wherein the chamber has a cross-section orthogonal to the average direction of the hydrodynamic flow which increases in the direction of the hydrodynamic flow, in the capture area.

Object 36. The fluidic system according to one of objects 31 to 35, wherein the means for applying a force field are means for applying a magnetic field.

Object 37. The fluidic system according to one of objects 31 to 35, wherein the means for applying a force field are means for applying an electric field.

Object 38. The fluidic system according to one of objects 31 to 37, wherein the means for determining comprise means for measuring a property in the capture area.

Object 39. The fluidic system according to one of objects 31 to 38, wherein the means for determining comprise means for measuring a property in a second chamber in fluid connection with the chamber comprising the capture area.

Object 40. The fluidic system according to one of objects 31 to 39, wherein the means for measuring a property are means for measuring a force, a displacement, a pressure, a flow rate, a mass, a density, a porosity, a viscosity, an elasticity, a viscoelasticity, an optical density, a turbidity, a texture, an intensity property or a radiation absorption coefficient.

Object 41. The fluidic system according to one of objects 31 to 40, wherein the means for measuring a property are means for measuring the volume occupied by the particles in the capture area.

Object 42. The fluidic system according to one of objects 31 to 41, comprising means for biological or biochemical analysis, and preferably means for genetic analysis, proteomic analysis or measurement of metabolic activity, and more particularly preferably means for amplifying and/or hybridizing nucleic acid, for sequencing nucleic acid, for immunoagglutination or immunoadsorption assay by a bound enzyme.

Object 43. The fluidic system according to one of objects 31 to 42, comprising means for molecular amplification, and wherein the means for determining are means for detecting products of molecular amplification.

Object 44. The fluidic system according to one of objects 31 to 43, wherein the chamber comprising the capture area is without any filter which may retain the particles.

Object 45. A computer program which, when it is executed, makes it possible to implement the method according to one of objects 1 to 30.

Object 46. A set for detecting organisms in a liquid sample comprising:
    the fluidic system according to one of objects 31 to 44; and
    the computer program of object 45.

Object 47. A set for detecting organisms in a liquid sample comprising:
    the fluidic system according to one of objects 31 to 44; and
    the particles to which the organisms are capable of binding.

Object 48. A set for detecting organisms in a liquid sample comprising:
    the fluidic system according to one of objects 31 to 44; and
    the growth medium.

Object 49. A set for detecting organisms in a liquid sample comprising:
    the fluidic system according to one of objects 31 to 44;
    the particles to which the organisms are capable of binding; and
    the growth medium.

Object 50. A set for detecting organisms in a liquid sample comprising:
the fluidic system according to one of objects 31 to 44;
the computer program according to object 45; and
the particles to which the organisms are capable of binding.

Object 51. An assembly for detecting organisms in a liquid sample comprising:
the fluidic system according to one of objects 31 to 44;
the computer program according to object 45;
the particles to which the organisms are capable of binding; and
the growth medium.

In another group of embodiments, the invention relates to the following objects, wherein a step (b) allowing the growth of the organisms is not necessarily provided.

Object 52. A method for detecting organisms in a liquid sample comprising providing a capture area including particles in a liquid medium and subjected to a hydrodynamic flow, wherein the organisms to be detected are capable of biding to these particles, the method further comprising the steps of:
circulating the sample through the capture area;
measuring a physical property of the capture area, during and/or after circulating the sample, so as to deduce therefrom the presence or the concentration or the nature of the organisms in the sample;
the particles being retained in the capture area as a fluidized bed during at least part of these steps.

Object 53. The method according to object 52, wherein the physical property measure is selected from among viscosity, viscoelasticity, volume, permeability and density properties.

Object 54. The method according to one of objects 52 to 53, wherein the measured physical property is a physical property of the particles as a fluidized bed.

Object 55. The method according to one of objects 52 to 53, wherein the measured physical property is a physical property of the particles as a compact bed.

Object 56. The method according to one of objects 52 to 55, further comprising a step of circulating a growth medium, preferably comprising nutrients for the organisms, for the organisms through the capture area, the step of measuring being carried out simultaneously with and/or after this step of circulating a growth medium.

Object 56a. A method for preparing organisms from parent organisms present in a liquid sample, comprising providing a capture area including particles in a liquid medium and subjected to a hydrodynamic flow, wherein the parent organisms are capable of binding to these particles, the method comprising the steps of:
(a) circulating the sample through the capture area and binding the parent organisms to the particles;
(b) circulating a growth medium through the capture area; and
(c) collecting, at the outlet of the capture area, organisms stemming from the division of the parent organisms;
the particles being retained in the capture area as a fluidized bed during at least part these steps.

Object 56b. The method according to object 56a, wherein step (c) is carried out without releasing the parent organisms bound to the particles.

Object 56c. The method according to one of objects 56a or 56b, wherein step (c) and step (b) are superimposed or alternate at least partly.

Object 56d. The method according to one of objects 56 to 56c, wherein the step of circulating a growth medium makes it possible to increase the number of organisms in the capture area or the number of collected organisms collected at the outlet of the capture area by a factor of at least 10, preferably at least a 100, or even at least a 1,000 or at least a 10,000 or at least a 100,000, relative to the number of organisms present in the initial sample.

Object 57. The method according to one of objects 52 to 56d, wherein the particles are retained in the capture area as a fluidized bed during part, and preferably during the totality, of the step of circulating the sample.

Object 58. The method according to one of objects 52 to 57, which is a method for detecting according to object 52, and wherein the particles are retained in the capture area as a fluidized bed during part, and preferably during the totality, of the step of measuring.

Object 59. The method according to one of objects 52 to 58, which is a method for detecting according to object 52, and wherein the particles are retained in the capture area as a compact bed during part, and preferably during the totality, of the measuring step.

Object 60. The method according to one of objects 52 to 59, wherein the velocity of the hydrodynamic flow decreases in the capture area, in the direction of the hydrodynamic flow.

Object 61. The method according to one of objects 52 to 60, wherein the retention of the particles in the capture area is obtained by applying a force opposed to the hydrodynamic flow.

Object 62. The method according to object 61, wherein the force opposed to the hydrodynamic flow decreases in the capture area in the direction of the hydrodynamic flow.

Object 63. The method according to one of objects 61 to 62, wherein the force opposed to the hydrodynamic flow is essentially aligned with the direction of the hydrodynamic flow.

Object 64. The method according to one of objects 61 to 63, wherein the force opposed to the hydrodynamic flow is a magnetic force, the particles being magnetic particles, preferably super-paramagnetic particles.

Object 65. The method according to one of objects 61 to 63, wherein the force opposed to the hydrodynamic flow is an electrostatic force, the particles being charged particles.

Object 66. The method according to one of objects 61 to 63, wherein the force opposed to the hydrodynamic flow is a gravity or centrifugal force, the particles having a density different from that of the surrounding liquid.

Object 67. The method according to one of objects 52 to 66, wherein the organisms to be detected, respectively the parent organisms, are capable of binding to the particles via ligands, preferably antibodies.

Object 68. The method according to one of objects 52 to 67, wherein the particles have an average size Dv50 from 1 nm to 500 μm, preferably from 50 nm to 100 μm, and more particularly from 1 μm to 50 μm.

Object 69. The method according to one of objects 52 to 68, wherein the organisms are selected from bacteria, unicellular or pluricellular parasites, fungi, eukaryotic cells and notably mammal cells or plant cells, and wherein, preferably, the organisms are selected from pathogenic organisms, stem cells and cancer cells.

Object 69a. The method according to one of objects 52 to 69, wherein the organisms are selected from endothelial cells, hematopoietic cells, epithelial cells, fetal cells, pluripotent cells, totipotent cells, and induced pluripotent stem cells.

Object 70. The method according to one of objects 52 to 69a, which is a method for detecting according to object 52 and wherein the measured property is the volume occupied by the particles in the capture area or a dimension of this occupied volume.

Object 71. The method according to one of objects 52 to 70, which is implemented in a microfluidic system.

Object 72. The method according to one of objects 52 to 71, further comprising a step of circulating a medium comprising a target area for the organisms through the capture area, optionally after the step of circulating the growth medium.

Object 73. The method according to object 72, for screening drugs or biocides, wherein the target agent is a potential drug or biocide.

Object 74. The method according to one of objects 52 to 73, wherein the sample is derived from the environment, or from a food product, or from a bodily fluid.

Object 75. A fluidic system for detecting organisms in a liquid sample, comprising:
  at least one chamber including at least one fluid inlet and one fluid outlet and including a capture area;
  means for circulating the liquid sample through the capture area;
  means for applying a force field in the capture area, said force field being configured to retain particles in the capture area as a fluidized bed when the capture area is subject to a hydrodynamic flow, the organisms to be detected being capable of binding to the particles;
  means for measuring a physical property of the capture area;
  means for determining the presence or the concentration or the nature of the organisms in the sample according to the result of this measurement.

Object 75a. The fluidic system for preparing organisms from parent organisms present in a liquid sample, and comprising:
  at least one chamber comprising at least one fluid inlet and one fluid outlet and including a capture area;
  means for circulating the liquid sample through the capture area;
  means for applying a force field in the capture area, said force field being configured for retaining particles in the capture area as a fluidized bed when the capture area is subjected to a hydrodynamic flow, the parent organisms being capable of binding the particles;
  means for collecting, at the outlet of the capture area, organisms stemming from the division of the parent organisms.

Object 75b. The fluidic system according to object 75, wherein the means for determining the presence or the concentration or the nature of the organisms present in the sample include means for collecting, culturing or multiplying organisms from the capture area.

Object 76. The fluidic system according to one of objects 75 to 75b, which is a microfluidic system.

Object 77. The fluidic system according to one of objects 75 to 76, wherein the force field is essentially aligned with the direction of the hydrodynamic flow in the capture area.

Object 78. The fluidic system according to one of objects 75 to 77, wherein the force field has a decreasing intensity in the direction of the hydrodynamic flow in the capture area.

Object 79. The fluidic system according to one of objects 75 to 78, wherein the chamber has a cross-section orthogonal to the average direction of the hydrodynamic flow which increases in the direction of the hydrodynamic flow, in the capture area.

Object 80. The fluidic system according to one of objects 75 to 79, further comprising means for circulating a growth medium through the capture area.

Object 81. The fluidic system according to one of objects 75 to 80, wherein the means for applying a force field are means for applying a magnetic field.

Object 82. The fluidic system according to one of objects 75 to 80, wherein the means for applying a force field are means for applying an electric field.

Object 83. The fluidic system according to one of objects 75 to 82, which is a fluidic system for detecting according to object 75, and wherein the means for measuring the property are means for measuring viscosity, viscoelasticity, volume, permeability and density.

Object 84. The fluidic system according to one of objects 75 to 83, which is a fluidic system for detecting according to object 75, and wherein the means for measuring the property are means for measuring the volume occupied by the particles in the capture area.

Object 85. The fluidic system according to one of objects 75 to 84, wherein the chamber including the capture area is without any filter which may retain the particles.

Object 86. A computer program which, when it is executed, makes it possible to implement the method according to one of objects 52 to 74.

Object 87. A set for detecting organisms in a liquid sample comprising:
  the fluidic system according to one of objects 75 to 85; and
  the computer program according to object 86.

Object 88. A set for detecting organisms in a liquid sample comprising:
  the fluidic system according to one of objects 75 to 85; and
  the particles to which the organisms are capable of binding.

Object 89. A set for detecting organisms in a liquid sample comprising:
  the fluidic system according to one of objects 75 to 85; and
  a growth medium.

Object 90. A set for detecting organisms in a liquid sample comprising:
  the fluidic system according to one of objects 75 to 85;
  the particles to which organisms are capable of binding; and
  a growth medium.

Object 91. A set for detecting organisms in a liquid sample comprising:
  the fluidic system according to one of objects 75 to 85;
  the computer program according to object 86; and
  the particles to which the organisms are capable of binding.

Object 92. A set for detecting organisms in a liquid sample comprising:
  the fluidic system according to one of objects 75 to 85;
  the computer program according to object 86;
  the particles to which organisms are capable of binding; and
  a growth medium.

BRIEF DESCRIPTION OF THE FIGURES

FIG. 1 schematically shows an embodiment of the microfluidic system according to the invention.

DESCRIPTION OF EMBODIMENTS OF THE INVENTION

Figure 2I:
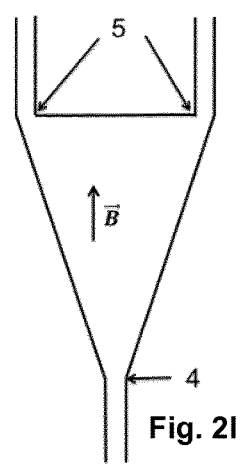
FIGS. 2A to 2Q schematically show various possible forms for the chamber of a microfluidic system according to the invention.

The invention is now described in more detail and in a non-limiting way in the following description.

Capture Area

The invention is based on the implementation of a capture area in a chamber of a fluidic system, for retaining particles therein while circulating fluids through the capture area (so as to generate a flow in the capture area, i.e. a hydrodynamic flow).

Thus, the fluidic system of the invention includes means for applying a force field in the capture area, said force field being configured for retaining the particles in the capture area.

By way of language simplification, in the whole description, by "force opposed to the hydrodynamic flow" is meant a force or a combination of forces, exerted on at least one particle, and opposed to the force(s) exerted on this particle by the hydrodynamic flow.

The force field may be electric, dielectric, electromagnetic, magnetic, gravitational (from gravity) or centrifugal. Preferably, it is magnetic. In some embodiments, the means for applying the force field are associated with a particular shape of the capture area.

The application means may notably comprise a magnetic system defining, in the capture area, a magnetic field having a gradient and capable of retaining the (magnetic) particles in the capture area.

The magnetic system may comprise one or several electromagnets, or one or several permanent magnets, or one or several polar pieces, or a combination thereof.

The obtained magnetic field may thus have, in at least one portion of the capture area, a gradient comprised from 10 T/m and 10000 T/m, preferably from 10 T/m to 5000 T/m, and more particularly preferably from 100 T/m to 1000 T/m.

Alternatively, the fluidic system of the invention may comprise an electrical system defining, in the capture area, an electric field capable of retaining the (charged) particles in the capture area.

The electrical system may in particular comprise at least two electrodes. The electrodes may, for example, be in contact with the capture area. The electrodes may also be in contact with a liquid in fluidic connection between the capture areas, in ancillary tanks.

Alternatively, the fluidic system of the invention may comprise an electrical system defining, in the capture area, an electric field having a gradient capable of retaining (dielectric) particles in the capture area.

The electrical system may in particular comprise one or several electrodes. The electrodes may also be in contact with the capture area. The electrodes may also be in contact with a liquid in fluid connection with the capture area, in ancillary tanks. The electrodes may also be located in the vicinity of the capture area, but separated from it by an insulator: this alternative is preferred when the electric field has an alternating component.

When an electrical system is used, it may generate a DC, alternating, pulsed electric field, or a combination of a DC component and a non-DC component. The electric field in at least a portion of the capture area (preferably in the whole of the capture area) may notably have an amplitude from 1 to 10 V/cm, or from 10 to 100 V/cm, or from 100 to 1000 V/cm; in other cases, and notably in the presence of insulated electrodes from the chamber, or when the electric field has a gradient, the amplitude may be from 1000 V/cm to 10,000 V/cm, or from 10,000 to 100,000 V/Cm.

It is also possible to combine together the magnetic and electrical systems described above.

The capture area may also be oriented in the gravity field so that the flow of the fluid in the capture area is oriented from the bottom to the top. Particle retention may then be achieved when the particles have a density greater than the circulating fluid.

Alternatively, the capture area may be oriented in the gravity field so that the flow of the fluid in the capture area is oriented from the top to the bottom. Particle retention may then be achieved when the particles have a density less than that of the circulating fluid.

It is also possible to carry out a rotation of the device, in order to generate within the chamber a centrifugal force. The retention of the particles may then be obtained when the circulating fluid flows in a direction opposite to the centrifugal force and the particles are denser than the circulating fluid.

The magnetic, electrostatic, gravity or centrifugal force, opposed to the flow of fluid, has the effect of retaining the particles in the capture area.

This force may be generated from respectively a difference in magnetic or electrical susceptibility, or a from a conductivity difference or from a density difference between the particles and the surrounding fluid.

The amplitude of the force opposed to the flow may comprise a continuous component. It may also comprise an alternating component.

The presence of an alternating component is preferred when dielectric particles are used, or when the force is an electric force produced by insulated electrodes of the capture area, or both.

The frequency of the alternating component may for example have a value from 1 to 100 Hz; or from 100 Hz to 10 kHz; or from 10 kHz to 1 MHz; or from 1 to 100 MHz.

The force fields opposed to the flow may be essentially stationary during one or some steps of the method or during the entire method; i.e. in each point of the capture area, the direction and amplitude of the force does not essentially vary over time. When the force has an alternating component, the absence of variation in direction and amplitude overtime is evaluated over a characteristic duration of at least 100 times the period of the alternating component.

The force field may also be non-stationary; i.e. at some points at least in the capture area, the force varies in amplitude and/or direction during the method.

If it is a magnetic force, the variation may be obtained either by varying a current in a coil, or by displacing magnetic or magnetizable media, for example by displacing a permanent magnet or a ferrofluid, or a magnetic shunt.

If it is an electric or electrostatic force, the variation may be obtained by changing a potential between two terminals of a generator.

If it is a gravity or centrifugal force, the variation may be obtained either by varying the tilt of the capture area relative to the orientation of the gravity field, or by varying a speed of rotation.

The force opposed to the flow may have a gradient in the capture area, i.e. the amplitude of the force may vary depending on the position in the capture area.

The force gradient in the capture area may be a monotonous gradient, i.e. the amplitude of the force varies in a monotonous way from one end to the other of the capture area. Preferably, the amplitude of the force decreases in at least a portion of the capture area (preferably in the whole capture area), in the direction of flow of the fluid.

The direction of the force is preferably the same (or essentially the same) in the whole capture area. In a more particularly preferred manner, it is essentially aligned with the direction of flow of the fluid.

Alternatively, the direction of the force may be transverse relative to the direction of the flow of the fluid, or have a variable orientation relative to the direction of the flow of the fluid, or have a variable orientation depending on the position in the capture area.

As is described in more detail below, depending on the geometry of the chamber and the nature of the force used for retaining the particles, it is possible to obtain a general orientation of the force approximately aligned with that of the flow, without this alignment being necessarily obtained strictly in the whole chamber, on the one hand because of the divergence of the force field (for example the divergence of the magnetic field imposed by the shape of the magnets used), and on the other hand because of flow phenomena inherent to hydrodynamics laws, like the presence of non-flow conditions on the edges of the chamber, and the presence of a Poiseuille profile. This is why this notion of alignment is understood in a general manner and not necessarily in an absolute manner.

Moreover, it may be advantageous in some cases to obtain a force field having a direction slightly different from that of the flow in order to promote the recirculation of particles in the chamber in the fluidized bed condition.

Fluidized Bed and Compact Bed

According to an embodiment, at least one of steps (a) to (c), and preferably two or three and more preferably all of these steps, are carried out at least partly in a so-called fluidized bed condition, i.e. the particles are in motion relative to each other while remaining collectively contained in the capture area and subjected to the circulation of a fluid (in this case a liquid).

The fluidized bed is obtained by subjecting the particles to a force opposed to the hydrodynamic flow of the fluid through the capture area.

This force is preferably a magnetic force, but may alternatively be an electric, gravity (or weight) or centrifugal force. Combinations of these forces are also possible.

The fluidized bed is preferably a dense but non-compact bed. Thus, the particles move relative to each another.

A compact condition is defined as a condition in which the particles are in permanent or quasi-permanent contact with neighboring particles. A dense but non-compact condition is a condition in which the particles come into contact with each other occasionally, but in which the particles are predominantly in contact with the fluid and not with other particles (the average distance between particles being however preferably less than 100 times, or 50 times, or 20 times, or 15 times, or 10 times, or 5 times, or 3 times the average size of the particles).

Thus, the dense but non-compact condition which is obtained in the fluidized bed generally corresponds, for spherical or approximately spherical particles, to a volume fraction occupied by the particles of 0.01 to 0.3 in the capture area, for example from 0.01 to 0.05 or alternatively from 0.05 to 0.3.

For non-spherical particles, and notably for very elongated particles, the dense but non-compact condition which is sought within the scope of the invention may correspond to a smaller volume fraction, for example from 0.001 to 0.1, since these particles interact more easily with each other.

According to an embodiment, some of the steps of the method of the invention are at least partly carried out in the non-fluidized (or compact) state, in other words a state in which the particles are essentially immobile relative to each other. For example, the volume fraction occupied by the particles in the non-fluidized or compact particle bed may be from 0.4 to 0.6 (most particularly for spherical or quasi-spherical particles).

Switching between the fluidized state and the non-fluidized state may notably be carried out by a change in flow rate of the fluid in the capture zone.

Thus, the fluid flow rate is advantageously controlled during at least one step, and preferably during several steps of the method or all the steps of the method.

Generally, flow rate values with which the particles are in a compact state are 5 to 50 times, or even up to 500 times lower than the flow rate values with which the bed of particles is in a fluidized, dense but non-compact condition.

The fluid flow rate in the capture area may assume different values during the method. Preferably, these values follow a pre-established sequence, correlated with the execution of at least some of steps (a) to (c).

Alternatively, switching between the fluidized and non-fluidized states may be carried out by modifying another operational parameter other than the fluid flow rate, and notably the force opposed to the flow. Thus, this operational parameter may be an electric field, a current, a magnetic field, a mechanical vibration intensity, a pressure, etc.

The application of a mechanical vibration may also contribute to controlling the fluidized or non-fluidized nature of the particles in the capture area, independently or in combination with the variation of the flow rate or of the force opposed to the flow.

Particles

Particle sizes indicated in the application are average sizes (Dv50).

Generally, the particle size is adapted according to the dimensions of the fluidic system used, and to the contemplated fluid flow rates.

The particles may notably be millimetric, i.e. have a size ranging from 1 mm to 10 mm; or micrometric, i.e. have a size ranging from 1 µm to 1 mm; or nanometric, i.e. have a size ranging from 1 nm to 1 µm.

Preferably, the particles have a size from 50 nm to 50 µm, more preferentially from 100 nm to 1 µm; or, alternatively, from 500 nm to 100 µm, more preferentially from 1 µm to 50 µm, or still preferentially from a 100 nm to 10 µm.

It is possible to use particles having a monomodal or multimodal distribution.

For example, particles having a bimodal distribution may be used. According to some embodiments, this distribution includes both micrometric particles and nanometric particles, or several distinct types of micrometric, millimetric or nanometric particles.

Preferably, the particles implemented in the invention bear ligands allowing them to bind in a specific way to some organisms.

According to an embodiment, this specific binding may be achieved via recognition sites present at the surface of said organisms, or associated with said organisms.

According to another embodiment, the specific binding may be carried out indirectly. In this case, a specific ligand of a type of organism, bearing a secondary recognition site, is put in the presence on the one hand of the sample containing the organisms, and on the other hand of the particles.

By "ligand" is meant a species, a molecular set or subset, a function, a surface or volume element having an affinity for a recognition site. The affinity in question may notably be of a chemical, physical or biological nature. In particular, it may rely on an electrostatic, magnetic, biochemical, hydrophilic-hydrophobic interaction, on molecular imprinting, hybridization, supramolecular structure formation, aggregation, association by depletion, etc.

According to a preferred embodiment, the ligands are antibodies, directed against a surface antigen of the relevant organisms.

According to another preferred embodiment, the ligands have affinity for glycosylated elements present on the surface of the organisms, or elements of the extracellular matrix.

Also, according to some preferred embodiments, more than one type of ligands may be used, for example if the intention is to capture several types of organisms at one time.

The particles may be magnetic particles, preferably superparamagnetic particles, in particular when the force opposed to the flow for the generation of the fluidized bed is magnetic.

The particles may also be charged or dielectric, in particular when the force opposed to the flow for the generation of the fluidized bed is electrical.

The particles may have a difference in density relative to the fluid present in the capture area. For example, the particles may have a density greater than or equal to that of the fluid, preferably greater than or equal to 1.2 times the density of the fluid, or greater than or equal to 1.5 times the density of the fluid, or greater than or equal to 2 times the density of the fluid, or greater than or equal to 3 times the density of the fluid, or greater than or equal to 4 times the density of the fluid.

Alternatively, the fluid may have a density greater than or equal to that of the particles, preferably greater than or equal to 1.2 times the density of the particles, or greater than or equal to 1.5 times the density of the particles, or greater than or equal to 2 times the density of the particles, or greater than or equal to 3 times the density of the particles, or greater than or equal to 4 times the density of the particles.

The method of the invention is advantageously implemented with a smaller amount of particles than in the prior art, owing to the gain in sensitivity made possible by the invention.

Thus, according to some embodiments, the total mass of retained particles in the capture area is less than 1 g, preferably less than 100 mg, preferably further less than 10 mg, still preferably less than 1 mg, preferably still less than 100 μg, and in some cases less than 10, 5, 4, 3, 2 or even 1 μg.

Fluidic System of the Invention

Advantageously, the whole method of the invention is implemented in a same fluidic system, i.e. the fluidic system of the invention. This makes it possible to avoid transferring a fluid from one container to another via a passage in open air, or by pipetting, which increases risks of contamination, and makes the automation of the method more complex.

The fluidic system of the invention includes at least one chamber for the capture area, which is equipped with at least one inlet and one outlet for the fluid.

The fluidic system may include a single chamber or several chambers. When several chambers are used, they are then in fluidic connection, i.e. they may exchange liquid in a continuous way by at least an intermediate conduit.

According to an embodiment, the fluidic system includes a second chamber in fluidic connection with the chamber including the capture area.

According to an embodiment, the fluidic system includes means for molecular amplification and for detection of the products from said molecular amplification, which in particular may be associated with the second chamber. Molecular amplification is described in more detail below.

The portion of the fluidic system in which the fluids circulate is preferably monolithic, i.e. consists of a single material. Other materials may be used for the other elements of the fluidic system, such as electrodes, magnets, connectors, adhesives, attachment elements, etc.

Preferably, the chamber including the capture area does not include any filter at the inlet and at the outlet which may retain the particles. In the prior art, filters are used for retaining particles, which entails risks of clogging in the presence of fluids containing contaminants such as debris or others which may have a larger size than that of the organisms to be detected or the particles.

The fluidic system of the invention may include a plurality of identical or different chambers, in order to provide parallel, serial or mixed operation (with parallel circuits including chambers in series, or circuits in series including chambers in parallel).

The different chambers may be supplied with samples, particles and identical or different media.

The system of the invention further advantageously includes one or several tanks, and in particular at least one tank containing the growth medium, one tank for the sample, one tank for the particles, optionally one tank for a washing solution, and optionally tanks for additional fluids.

The chamber of the fluidic system of the invention including the capture area generally has a fluid inlet, a fluid outlet and a channel area which is widened relative to the inlet and the outlet. The optional other chambers of the fluidic system may also have a geometry of the same type.

The chambers may also have other shapes, such as, for example, cylinder shapes, parallelepiped shapes or more complex shapes. Advantageously, the chambers may include flow homogenization elements. These homogenization elements may be formed with multiple structures attached to the walls of the chamber, such as pillars, so as to create local obstacles to the flow and to prevent the development of a flow of the Poiseuille-type in the chamber.

The fluidic system of the invention, or parts of it, may be manufactured by 3D printing. Alternatively, the fluidic system of the invention or parts of it, may be manufactured by any techniques for shaping materials, such as machining, micro-machining, molding with pressure or by injection, microlithography, laser ablation, dry or wet etching.

The fluidic system of the invention, and notably the chambers described above, may be made of any kinds of materials, such as plastic materials, glass, metals. According to some preferred embodiments, the fluidic system includes at least one window allowing imaging or optical detection.

The fluidic system may consist of several elements assembled to one another. According to an embodiment, the element comprising the chamber which includes the capture area is removable relative to the remainder of the fluidic system. This may make it possible to use a single-use chamber with a capture area. The fluidic system of the invention comprises, in this case, means for achieving a connection of at least one fluidic inlet and one fluidic outlet of the removable element with orifices for fluid circulation integrated to the remainder of the fluidic system.

The fluidic system according to the invention advantageously includes means for regulating temperature, in particular in the capture area. These means may, for example, consist in a heating, or a cooling, or combined means for heating and cooling. As an example, these may be Pelletier modules, or a circulation of fluids in one or several ancillary circuits in thermal contact with said system. These may also be means for heating by a resistant layer, such as, for example, a layer of indium and tin oxide (ITO). Advantageously, these means are regulated by a temperature regulator. Advantageously, also, this temperature regulator uses the information provided by one or several temperature sensors integrated to the system.

Thus, temperature may be regulated, notably during step (b) of the method, in order to promote the growth of the organisms present in the capture area. A temperature of 20 to 60° C., preferably form 30 to 50° C., more particularly from 35 to 40° C., and for example of about 37° C., is preferred for some organisms.

Preferably, the fluidic system of the invention is transportable. It may for example weigh less than 50 kg, or less than 20 kg, or less than 10 kg.

Preferably, the fluidic system of the invention is portable. It may for example weigh less than 5 kg, or less than 1 kg.

According to other embodiments, the system according to the invention has no dimension greater than 50 cm, and preferably no dimension greater than 30 cm.

The capture area of the fluidic system, as well as the means making it possible to retain the particles in the capture area, were described above.

The fluidic system of the invention includes means for transporting fluids (and particles), which are described in more detail below.

The fluidic system of the invention also includes detection means, which are described in more detail below.

Microfluidic System

In a particularly preferred way, the fluidic system of the invention is a microfluidic system, i.e. a system comprising one or several microstructures on the surface of a substrate, which are elements adapted for containing and/or directing fluids. These microstructures have at least one dimension which is less than 1 mm, and in a more particularly preferred way less than 500 µm. In some cases, these microstructures may have at least one dimension of less than 200 µm, or than 100 µm, or than 50 µm, or than 20 µm, or than 10 µm, or than 5 µm, or than 2 µm or than 1 µm.

These microstructures may include closed volumes and in some cases have an open surface.

By channels (or micro-channels) is meant microstructures adapted for the circulation/flow of fluids. They are most often closed on the whole path of the fluid. The substrate is preferably a plate or wafer. The substrate is preferably essentially rigid, which means that it may be handled and attached so as to be maintained immobile, towards a detector, for example. It may be made of glass, silicon, ceramic, metal or a polymeric/plastic material. The substrate may be covered with a lid of the same nature, or with a flexible material, such as a silicone elastomer, for example polydimethylsiloxane. Alternatively, the substrate and of the lid may be made of a flexible material, such as a silicone elastomer, for example polydimethylsiloxane. It is also possible to use a fluorinated polymer such as those known under the name of "Dyneon". It is also possible to use a thermoplastic polymer such as an olefin polymer or copolymer, notably a cyclic olefin, polycarbonate, polymethyl methacrylate, polystyrene, polyethylene terephthalate. Transparent polymers are preferred, optionally in combination with glass.

The manufacturing of the microstructures of the microfluidic system may be based on micro manufacturing techniques, such as thin deposition techniques, photolithography, (chemical or plasma) etching, thermoforming, molding, molding by injection, and adhesive bonding. The deposition of a film may be carried out by centrifugation, by thermal oxidation, by chemical or physical vapor deposition (CVD and PVD), by low pressure CVD, by plasma-enhanced CVD, by spraying, etc.

The microfluidic system may be or comprise an on-chip laboratory.

The microfluidic system may include a network of channels, i.e. a plurality of channels positioned between the substrate and its lid, or entirely surrounded by the substrate, and which are in fluidic communication either with one another or with one or several fluid sources exterior to the system.

The microfluidic system may also include a series of channels, i.e. a set of a plurality of unconnected channels, or networks of unconnected channels, on the same substrate.

The microfluidic system may be connected to tanks of fluids or samples and to other ancillary devices through tubes or pipes or connectors (e.g. Y or X connectors), in order to bring fluids towards, or to collect the fluids from the system. Alternatively, these tubes or pipes and optionally the tanks and other ancillary devices may be considered as part of the microfluidic system.

It may be advantageous to use a microfluidic system with relatively high fluid flow rates with respect to the dimensions at stake, in order to combine a high sensitivity with small dimensions.

The flow rate of the sample may in particular be from 1 nL/min to 10 mL/min, preferred flow ranges being from 1 µL/min to 100 µL/min, from 100 µL/min to 1 mL/min and from 1 to 10 mL/min.

The capture area may have a volume ranging from 1 nL to 10 mL. Possible volume ranges are: from 1 mL to 10 mL, or from 100 µL to 1 mL, or from 10 µL to 100 µL, or from 1 µL to 10 µL, or from 100 nL to 1 µL, or from 10 nL to 100 nL, or even from 1 nL to 10 nL.

According to an alternative of the invention, the fluidic system of the invention may be a millifluidic system, i.e. it includes one or several channels for the flow of fluids, at least one dimension of which is less than 1 cm, preferably is comprised between 1 mm and 5 mm (no dimension being however less than 1 mm, as this is a case in a microfluidic system).

Transport of Fluids and Particles

In the method of the invention, the particles have to be brought to the capture area, and then various fluids have to circulate through the capture area, notably the investigated sample, and the growth medium. Other fluids may circulate through the capture area for intermediate washing steps, or for implementing the detection step (c). The particles generally have to be withdrawn from the capture zone, either for the purpose of the detection step (c), or after it.

According to the invention, the transport of the fluids (and particles) may be carried out by means of a fluid actuation system, which may notably comprise pumps, pressure controllers, vibrating elements, valves. In some alternatives, the transport of the fluids and/or particles may also be carried out at least partly by the effect of gravity or of a centrifugal force.

By way of pumps, it is notably possible to use micro manufactured pumps or external pumps, such as microfluidic control pumps, syringe pumps, peristaltic pumps, membrane pumps, piston pumps, rotary pumps.

Preferably, pumps without any pulses are used, such as pressure controlled microfluidic pumps. Such systems avoid hysteresis problems which may be encountered with pumping systems based on volume control, such as syringe pumps. Indeed, in the latter, each stopping of the flow tends to generate a compact stacking of magnetic particles towards the inlet of the channel, blocking the inlet of the channel and possibly leading to an accumulation of pressure and then to a bursting of the compact stack of particles and to the loss of particles when the flow rate is re-established.

The microfluidic pumps controlled by pressure, like for example the MFCS system from Fluigent, or the Mythos pump from Dolomite, make it possible to avoid the accumulation of excessive pressure, and to limit the above risks.

The system of the invention preferably includes a means for measuring pressure, or a means for measuring flow rate in the capture area, and a combination of means for measuring pressure and flow rate.

It is preferred to use systems in which the pressure is dynamically regulated by means of information from a flowmeter. This may make it possible to gradually increase pressure in order to increase or rapidly reduce the fluid flow rate through the particle bed in order to maintain the flow rate within predetermined limits and thereby avoid any bursting phenomenon of the particle bed.

Actually, with this embodiment, it is possible to stop the flow, or reduce the flow rate to a low value, while retaining the force field opposed to the flow, and applying a finite and controlled positive pressure at the inlet of chamber. Thus, the back flow of the particles upstream from the capture area is avoided.

The transport of the fluids and/or particles may also be carried out by applying an electric field, by generating electrophoretic, dielectrophoretic or electroosmotic forces. In particular, the flow of the fluids may be electroosmotic. It may be directly generated by the presence of electrical charges on walls of the fluidic system or on particles contained in the fluidic system (either in the capture area or out of the capture area).

When the transport of the fluids and/or particles is carried out by applying an electric field, the latter may be a DC, alternating, pulsed electric field, or have a DC component and a non-continuous component. It may notably have an amplitude from 1 to 10 V/cm, or of 10 to 100 V/cm, or from 100 to 1000 V/cm; in other cases, and notably in the presence of electrodes insulated from the fluids, or when the electric field has a gradient, the amplitude may be from 1,000 V/cm to 10,000 V/cm, or from 10,000 to 100,000 V/cm.

According to an embodiment, mechanical vibration is applied to the fluidic system of the invention, or to channels for bringing fluid towards the fluidic system. This vibration may notably have a frequency from 1 Hz to 10 Hz; or from 10 Hz to 100 Hz; or from 100 Hz to 1 kHz; or 1 kHz to 10 kHz; or from 10 kHz to 100 kHz; or from 100 kHz to 1 MHz. The mechanical vibration may be generated in a non-limited manner by an inertial vibrator including a piezoelectric element, a loudspeaker, an electromagnetic element, a rotary element or an alternating element.

The application of a mechanical vibration may make it possible to reduce the involuntary presence of gas bubbles in the fluid, and thereby improve the quality of the flow. It may also make it possible to induce a vibratory or alternative component in the flow, which may facilitate the control of the binding of the organisms to the particles notably by accelerating contact kinetics; or which may on the contrary, detach organisms possibly bound to the particles by non-specific affinity.

Within the scope of the method of the invention, continuous circulation periods of fluid may alternate with periods of stopping the fluid (which may notably make incubation or reaction steps possible). Periods of circulating a fluid at a first flow rate may also be alternated with periods of circulating a fluid at a second flow rate which is preferably at least 10 times, or at least 50 times less than the first flow rate.

Flow rate values which may be used are notably from 1 nL/min to 10 mL/min, and in particular from 1 μL/min to 100 μL/min.

Microfluidic System with Magnetic Capture

In a preferred embodiment, the fluidic system according to the invention is a microfluidic system allowing a magnetic capture of particles in the capture area owing to means for applying a magnetic field.

Making reference to FIG. 1, the microfluidic system 1 according to the invention may thus include at least one chamber 2 for a flow of a fluid with an inlet 4 and an outlet 5, as well as means for applying a magnetic field 6.

It may be in the form of an assembly comprising on the one hand the device for circulating fluids (micro-structured substrate including the chamber, and the pipes, tanks and other elements in fluidic connection therewith) and on the other hand means for applying a magnetic field, not necessarily fixed or attached to the device for circulating fluids.

The terms of inlet and outlet are selected with reference to the majority direction of the flow of the fluids (sample, growth medium, etc.). For the purposes of some procedures, one may however be led to transiently circulating some fluids in the opposite direction (from the outlet to the inlet), or between different inlets and outlets, for example for rinsing operations.

The chamber may include a plurality of inlets and/or a plurality of outlets, under the assumption that it is a branched channel.

Making again reference to FIG. 1, the chamber 2 includes the capture area 3, which is adapted for containing a bed of magnetic particles (notably as a fluidized bed).

The chamber 2 has a generally elongated shape, with a longitudinal axis 7 between the inlet 4 and the outlet 5.

Figure 2J:
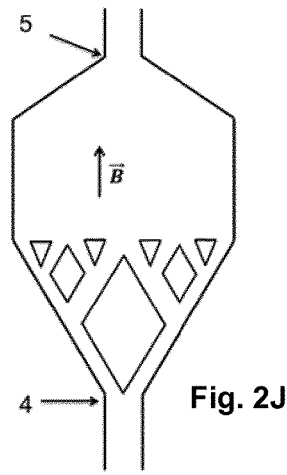
Figure 2K:
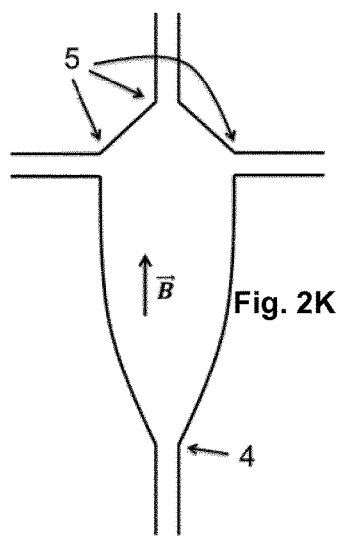
Figure 2L:
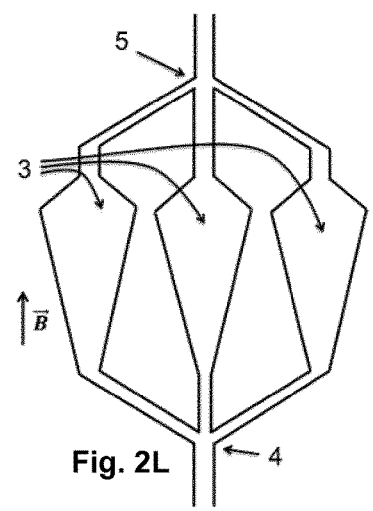
Figure 2M:
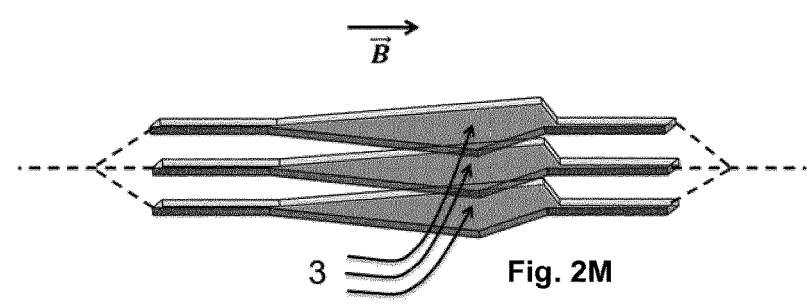
Figure 2N:
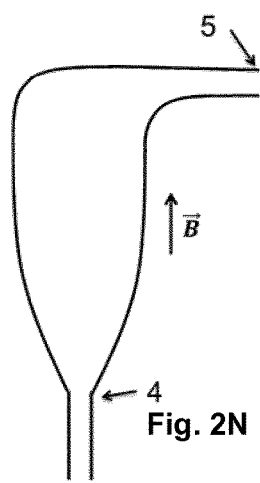

The longitudinal axis 7 is generally a straight line (at least in the capture area 3 of the chamber 2), as for example illustrated in FIG. 1, but it may in some cases consist of segments of straight lines or be curved if the chamber includes bends or curves or changes in direction (see, for example, FIG. 2N).

The longitudinal axis 7 of the chamber 2 generally corresponds to the average direction of flow of the fluid in the chamber (which may be defined as the direction of the average velocity vector of the fluid in the chamber, in a non-turbulent flow mode).

The longitudinal axis 7 may be an axis of symmetry of the chamber 2, or at least of the portion of the chamber 2 forming the capture area 3.

The transverse cross-section of the chamber is defined as the section cross-orthogonal to the longitudinal axis 7 of the chamber 2.

It is preferred that the transverse cross-section of the chamber 2 be greater than or equal to (preferably greater than) at any point to the transverse cross-section of the inlet 4 of the chamber; and/or that the transverse cross-section of the chamber 2 be greater than or equal to (preferably greater than) at any point than the transverse cross-section to the outlet 5 of the chamber 2.

According to the invention, the capture area 3 widens along the longitudinal axis 7, in the direction of flow, i.e. the transverse cross-section of the chamber 2 increases along the longitudinal axis 7 from the inlet 4 to the outlet 5 of the chamber 2.

For example, the chamber may have a conical shape along its longitudinal axis. Alternatively, and preferably for better ease of manufacturing, the chamber may have a rectangular transverse cross-section, having a height (or thickness, in the direction perpendicular to the plane of the substrate) and a width, the width increasing in the direction of the flow (the height remaining constant), or the height increasing in the direction of flow (the width remaining constant), or the width and height increasing in the direction of flow.

The chamber advantageously has a constant height (thickness) for better ease of manufacturing.

Generally, the chamber may have a circular, oval, triangular, square, rectangular or other transverse cross-section (including different shapes at different positions along the longitudinal axis), and it may be open on one side towards the external environment (the top side), be it over the whole length of the chamber or only a portion thereof. The chamber may also preferably be closed, except for the inlet and the outlet.

The chamber may be a capillary channel.

The increase in transverse cross-section is preferably continuous, and for example linear.

Downstream from the capture area, the chamber may include a downstream area, which is therefore located between the capture area and the outlet. This downstream area may have a constant or increasing transverse cross-section, but also preferably a transverse cross-section which decreases towards the outlet, in order to provide the required transition towards the outlet which generally has a reduced dimension.

Preferentially, the capture area has a generally elongated shape. Preferentially, the entire chamber has a generally elongated shape.

Preferentially, the length of the chamber and/or the length of the capture area is greater than the maximum dimension of the chamber in its transverse cross-section, and notably by a factor of at least 2 or at least 3 or at least 5, and which may range up to 20, 100 or 500.

The capture area may be branched in some cases, in which case the transverse cross-section is formed by the sum of the transverse cross-sections of the different branches.

The maximum dimension of the transverse cross-section may for example be, depending on embodiments, less than or equal to 5 mm, or 1 mm, or 500 µm, or 200 µm, or 100 µm, or 60 µm, or 50 µm, or 40 µm, or 30 µm, or 20 µm, or 10 µm, or 3 µm, or 1 µm, or 300 nm, or 100 nm, or 30 nm, or 10 nm.

Further, the ratio of the length of the capture area (dimension along the longitudinal axis) over the maximum dimension of the transverse cross-section may for example be from 1 to 500, and preferentially from 2 to 50, more particularly from 3 to 5, from 5 to 20 or more rarely from 20 to 50.

The height or thickness of the chamber may generally range from 1 µm to 5 mm, preferably from 10 µm to 100 µm or from a 100 µm to 1 mm.

The capture area of the chamber may have a volume ranging up to 10 mL. However, it is preferred that it has a small volume, for example from 1 mL to 10 mL, or from 100 µL, to 1 mL, or from 10 µL or from 100 µL, or from 1 µL to 10 µL, or from 100 nL to 1 µL, or from 10 nL to 100 nL, or even from 1 nL to 10 nL. Volumes of less than 10 µL are preferred.

It may be suitable that the chamber, and notably its capture area or an area of the chamber located downstream of the capture area, to be closed on one of its sides by a transparent material having a thickness compatible with an optical observation, and notably a high resolution microscopic observation, forming a window. The thickness of the window is preferably less than 500 µm, notably less than 200 µm, in particular for a microscopic observation.

In some other embodiments, for example preferred for low-cost applications, microscopic observation is unnecessary, and the chamber in this case has walls of a thickness greater than 200 µm, or even greater than 500 µm.

Figure 2O:
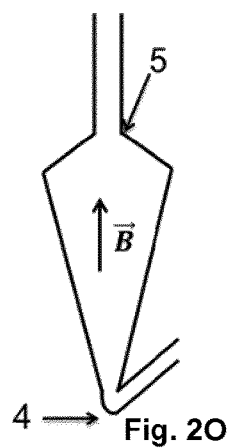
Figure 2P:
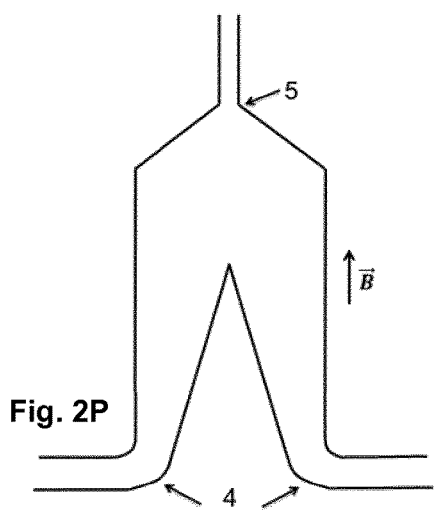

FIGS. 2A to 2P illustrate various alternatives for the shape of the chamber described above, the inlet (or inlets) being referenced as 4 and the outlet (or outlets) being referenced as 5. The general direction of the magnetic field is illustrated by a vector on the diagrams.

FIG. 2A shows a chamber with a single inlet 4 and a single outlet 5, a constant thickness, a length L, and a width I which linearly increases from a minimum at the inlet 4, up to a maximum (less than the length L), and then linearly decreases down to the outlet 5. The global shape of the chamber is therefore that of an asymmetrical rhombus. The capture area 3 is located between the inlet 4 and the area of the chamber of maximum width.

FIG. 2B shows an alternative with a width which varies in a non-linear manner. Further, a window 15 (as described above) is provided on an upper or lower surface of the chamber, and/or a window 16 is provided downstream from the chamber.

FIG. 2C shows an alternative wherein the chamber has a three-dimensional, cone-shaped, widening.

FIG. 2D shows an alternative wherein the chamber has a three-dimensional widening, of a pyramidal shape.

FIG. 2E shows an alternative of a chamber close to that of FIG. 2B.

FIG. 2F shows an alternative of a chamber close to that of FIG. 2A, but with an essentially symmetrical rhombus shape.

FIG. 2G shows an alternative with an inlet 4 branching into three supply channels, upstream from the chamber.

FIG. 2H shows an alternative with four outlets 5, opening onto parallel respective downstream channels. In this alternative, the width of the chamber continuously increases from the inlet 4 to the outlets 5, without passing through a maximum, and the shape of the chamber as seen from top is therefore globally triangular.

FIG. 2I shows an alternative close to that of FIG. 2H, with only two outlets 5.

FIG. 2J shows an alternative with multiple branches downstream from the inlet 4, of the delta type.

FIG. 2K shows an alternative with three outlets 5, opening into downstream channels in divergent directions.

FIG. 2L shows an alternative wherein the chamber is branched into three branches between the inlet 4 and the outlet 5, positioned parallel in the same plane of the substrate of the microfluidic system, each branch including a capture area 3 (with widening of the branch from the inlet 4 to outlet 5).

FIG. 2M shows an alternative wherein the chamber is branched into three branches between the inlet 4 and the outlet 5, superposed in different thicknesses of the substrate of the microfluidic system, each branch including a capture area 3 (with widening of the branch of the inlet 4 to the outlet 5). This arrangement notably makes it possible to increase the global flow rate of the system from a unique shape, while retaining its characteristics.

FIG. 2N shows an alternative with a chamber forming a bend at the outlet 5.

FIG. 2O shows an alternative with a chamber forming a bend at the inlet 4.

FIG. 2P shows an alternative with a chamber including two inlets 4, the chamber including two branches which join up, and a single outlet 5 downstream from the junction point.

Figure 2Q:
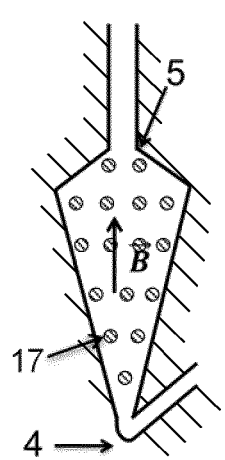
Figure 3:
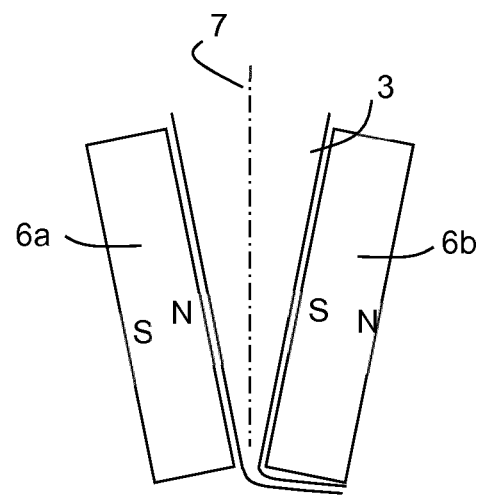
FIG. 3 schematically shows a detail of an embodiment of the microfluidic system according to the invention.

FIG. 2Q shows (in a horizontal cross-section) an alternative with a chamber including elements for homogenization of the flow 17.

Referring again to FIG. 1, the invention provides means for applying a magnetic field 6, the applied magnetic field being essentially parallel to the longitudinal axis 7 of the chamber 2. In the figure, the orientation of the magnetic field is illustrated with an arrow.

In particular, the direction of the magnetic field at any point of the capture area 3 of the chamber 2 forms an angle less than or equal to 20°, or than 15°, or than 10° or than 5°, relative to the longitudinal axis 7 of the chamber 2; or further the direction of the magnetic field at any point of the capture area 3 of the chamber is parallel to the longitudinal axis 7 of the chamber.

Alternatively, the average vector of the magnetic field may be taken into consideration on a transverse cross-section of the chamber. This average vector forms an angle of less than or equal to 20°, or 15°, or 10°, or 5° with the longitudinal axis of the chamber, along the capture area of the chamber; or this average vector is parallel to the longitudinal axis of the chamber along the capture area.

This alignment of the magnetic field on the geometry of the chamber is also expressed in terms of alignment of the magnetic field with the fluid flow.

Thus, according to preferred embodiments:
the direction of the magnetic field at any point of the capture area of the chamber forms an angle less than or equal to 20°, or 15°, or 10°, or 5°, relative to the velocity vector of the fluid in the chamber at this point (in a non-turbulent flow);
the average magnetic field vector on a transverse cross-section of the chamber forms an angle of less than or equal to 20° or 15° or 10° or 5° relative to, or is parallel with, the average velocity vector of the fluid on said transverse cross-section along the capture area of the chamber.

Another essentially equivalent way of defining the parallelism of the magnetic field relative to the capture area of the chamber (subject to a few divergences or small local or time variations) consists in imposing that the magnetic field lines in the capture area of the chamber are essentially aligned with the hydrodynamic field lines in this capture area (in a non-turbulent flow), i.e. the angle between these respective field lines is less than or equal to 20°, or 15°, or 10°, or 5° at any point in the capture area.

The component of the magnetic field in the plane of the substrate perpendicular to the longitudinal axis 7 of the chamber 2 (lateral component) is at any point less than 30% or less than 20% (or less than 15% or less than 10% or less than 5%) of the component of the field along the longitudinal axis and the field is therefore oriented almost along the longitudinal axis 7 in the whole chamber 2. It should be noted that the presence of a decrease in the field along the longitudinal axis implies, by conservation of the flow, a divergence of the field, and that at some points, and notably towards the walls of the chamber, the field therefore has a non-zero lateral component.

This magnetic field may be generated by means of a permanent magnet, or of an electromagnet, or of a combination latter, optionally associated with a polar part formed with a soft magnetic material able to direct the field lines. Preferably, such a polar part is without any microstructure which may generate a plurality of local maxima of the magnetic field.

In the case of the use of an electromagnet without any coil, for example an electric coil, it is considered that the poles of the electromagnet are the two planes corresponding to the inlet and the outlet of the magnetic flux in the coil.

In the following, unless indicated otherwise, the permanent magnets and the electromagnets will be designated under the generic term "magnet".

In some embodiments, the magnetic field may be activatable or adjustable. In particular, it is advantageous to be able to modify the intensity (amplitude) of the magnetic field, without modifying its orientation (i.e. its direction, or the shape of the field lines).

According to an embodiment, the invention provides positioning of the magnet with its north/south polar axis essentially aligned with the longitudinal axis of the chamber. It is preferred to position the magnet on the side of the inlet of the chamber. This differs from geometries proposed in the state of the art wherein the magnets or electromagnets are positioned on the sides of the chamber or above and/or below the chamber, i.e. in any case close to the walls of the chamber essentially parallel with the direction of flow.

The face of the polar portion or of the permanent magnet facing the capture chamber may, depending on embodiments, be flat, or have various shapes. For example, it may be curved according to one or several directions, or even in some cases include one or several edges. It is preferably configured so as to generate a field which gradually and continuously decreases within the capture area. If there are edges, they should preferably have an obtuse angle, preferably greater than 60°, or greater than 80°. Also, if said face of the polar portion or of the magnet is curved and convex (bowed), it preferably has a radius of curvature greater than the length of the portion of the capture area intended to receive and retain magnetic particles. The adjustment of the shape of the polar part (or of the magnet) may make it possible to modulate the divergence of the magnetic field and therefore optimize the performance of the system, depending on the shape of the chamber and of its capture area, either by trial and error, or by numerical simulation.

Thus, the magnetic field provided in the invention preferably varies in a continuous and monotonous (decreasing) way along the longitudinal axis or the direction of flow, from the inlet to the outlet, in the capture area. Any local maximum intensity is thereby avoided, which may lead to local and therefore compact trapping of magnetic particles.

Non-linear variations or even non-continuous variations in the transverse cross-section of the chamber, of the average flow velocity of the fluid, and of the intensity of the magnetic field are possible in some cases, depending on the desired flow rates and residence times of the fluid.

Figure 4:
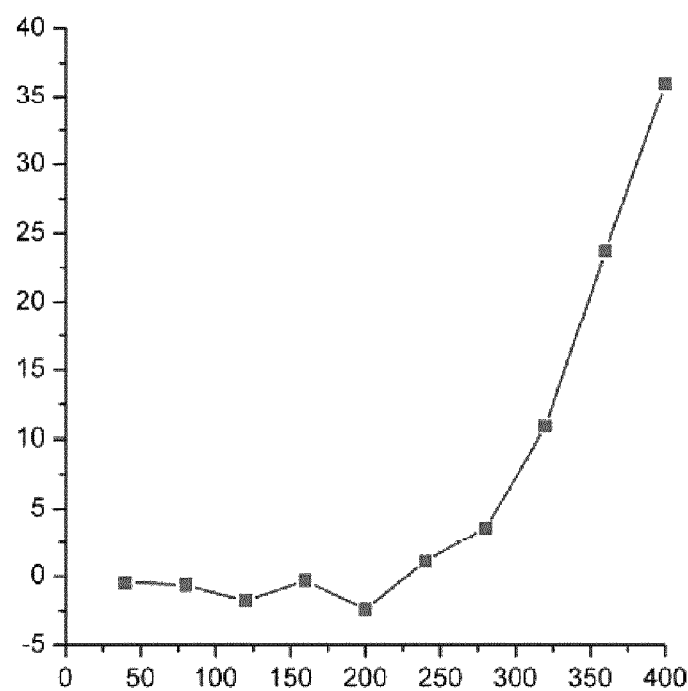
FIG. 4 is a graph showing the average fluorescence of a bed of particles having captured bacteria (on the Y-axis, in arbitrary units) according to the incubation period of the particles with a growth medium, in a microfluidic system of the invention (on the X-axis, in minutes). Reference will be made to example 2 for more details.

According to an alternative embodiment, illustrated in FIG. 4, the magnetic field is essentially orthogonal to the longitudinal axis 7 of the chamber, instead of being essentially parallel. For example, the means for applying a magnetic field 6 may comprise a first magnet 6a and a second magnet 6b, located on either side of the capture area 3 of the chamber and facing each other, the north pole of the first magnet 6a being directed towards the chamber and the south pole of the second magnet 6b being directed towards the chamber.

The face of the north pole of the first magnet 6a is not parallel to the face of the south pole of the second magnet 6b, so that the intensity of the magnetic field decreases in the capture area 3 along the direction of flow (the faces of the magnets are closer to the upstream side than to the downstream side in the capture area 3).

In the illustrated example, the capture area 3 is delimited by sides of the chamber, which are non-parallel and which run apart in the direction of flow, and the magnets 6a and 6b are positioned parallel to these sides of the chamber.

By correctly adjusting the intensity of the magnetic field and the fluid flow rate, an equilibrium is attained between the magnetic and hydrodynamic forces making it possible to maintain the magnetic particles in the capture area.

The microfluidic system may also include a plurality of other channels, of additional inlets and outlets and of valves, as well as tanks of the different fluids used.

In the example illustrated in FIG. 1, the microfluidic system 1 includes a supply channel 8 fluidically connected to the inlet 4 of the chamber 2 described above. This supply channel 8 includes a first inlet 9, a second inlet 10 and a third inlet 11, wherein each of these inlets may be connected to a tank of a distinct fluid and/or to means for controlling pressure. At the outlet 5 of chamber 2 described above is connected a secondary conduit 13, itself connected to an outlet 12 which may be connected to a fluid tank and/or to means for controlling pressure.

In the illustrated example, the supply channel 8 forms a bend with an angle greater than 90° with the main chamber 2, which may be advantageous for bringing magnetic particles from a tank to the chamber 2.

The regular nature of the curvature, combined with the small cross-section of the channel in this area in which the magnetic field is not directed along the axis of the channel, and which therefore does not have the nature of a capture area according to the invention, makes it possible to prevent some magnetic particles from remaining trapped in this section of the channel, and makes it possible on the contrary to force most, and in the most favorable cases, all, of the magnetic particles contained in the channel, to proceed to the capture area 3 and to remain there. But any other conformation, notably in the alignment of the chamber 2, is possible. Also, in the illustrated example, the secondary conduit 13 is aligned along the longitudinal axis 7 of the chamber 2, but any other conformation is possible.

The microfluidic system of the invention may also be associated with, or may comprise, any computer, electronic or electric controller, in order for example to control the temperature and the operation of the different components, to automate the operations and record data.

According to an embodiment, the system according to the invention includes a secondary conduit having a higher hydraulic resistance than that of the chamber 2, either upstream (before the inlet of the chamber) or downstream (after the outlet of the chamber), in series relative to the (main) chamber described above. This embodiment allows a better control of the flow in the chamber.

In the example of FIG. 1, the secondary conduit 13 has a hydraulic resistance greater than that of the chamber 2, by an appropriate selection of its length and of its transverse cross-section (which may for example be equal to, or less than or equal to, the transverse cross-section of the chamber 2 at its outlet 5).

Preferably, the hydraulic resistance of the secondary conduit is at least twice or at least 5 times, or at least 10 times, for example between 10 times and 100 times that of the capture area of the chamber described above (in the absence of magnetic particles).

The secondary conduit may be a secondary channel formed in the same substrate as the chamber, or it may be a tube or pipe connected to the chamber.

Steps of the Method

The steps (a) to (c) of the method may be sequential (and optionally separate in time); in other words, step (a) is carried out in its entirety; and then step (b) is carried out in its entirety; and then step (c) is carried out in its entirety. Alternatively, the steps may be at least partly carried out in a simultaneous way.

For example, detection step (c) may be carried out concomitantly with step (a) and/or step (b). This for example allows measurements of the change in the number or in the size of the organisms during the method.

In such an embodiment, the result of the detection may be used for modifying step (a) and/or step (b), and notably for modifying the duration of the step, or the liquid flow rate during the step, or the value of another operational parameter as defined above.

According to an alternative, the detection method is applied with several samples, in which case several samples are injected into the capture area during step (a).

Growth of Organisms

During step (b), a growth medium is circulated in the capture area. This medium makes it possible to control the growth of the organisms of the sample optionally captured in the capture area during step (a) by binding to the particles.

Preferably, it is a nutritive medium or a culture medium.

The growth medium may be specific to a type of particular organism. Alternatively, this may be a non-selective medium.

By "growth" is meant a metabolic amplification of the organisms, i.e. a vital process by which the number or the mass or the number of cells (in the case of pluricellular organisms) of the organisms increases. This growth may correspond to a development, a culture, a division, a proliferation or an expansion. Preferably, when the organisms are individual cells, the growth corresponds to a succession of cell divisions.

Advantageously, at least some of the organisms generated by cell division bind to the particles, during step (b).

In some embodiments, before, after or during step (b), the optionally captured organisms are put into the presence of species towards which the reaction of said organisms is sought to be studied.

These species may notably be potentially toxic agents or on the contrary stimulators of growth or division, signaling agents triggering some specific metabolic reactions, or further substrates towards which one seeks to determine the metabolization potential of said organisms.

These species may also be other organisms. Thus, the invention makes it possible to achieve a co-culture. In particular, it is possible to produce a co-culture of eukaryotic cells, notably mammalian or plant cells, in the presence of other organisms, and notably of bacteria or fungi. A particular application is that of the study of bacteriomas.

Preferably, no oxygenation of the growth medium is provided. Thus, the presence of gas bubbles is avoided, which allows a more regular and better controlled fluid flow.

During step (b), the possibly captured organisms in the capture area may undergo an exponential growth. This provides a wide dynamic range for detection and makes the invention very advantageous, for example as compared with culture methods on a solid medium of the prior art.

The sample used in step (a), before growth, may comprise target organisms in a concentration of less than 1 million per ml (or per gram), preferably less than 1000 per ml (or per gram), still preferably less than a 100 per mL (or per gram), still preferably less than 10 per mL (or per gram), and even possibly less than 1/mL (or per gram) or less than 1 organism per 10 mL or for 10 g), or less than 1 organism for 25 mL (or for 25 g).

The sample used in step (a) before the growth, may contain a total number of organisms to be detected of less than 100,000, preferably less than 10,000, still more preferably less than 1,000, still preferably less than 100, still preferably less than 50, still preferably less than 20, still preferably less than 10, and in some applications preferably less than 5, 4, 3, 2 or even it may contain a single organism. The invention thus provides particularly interesting detection sensitivity in very diluted samples.

Preferably, the amount of organisms to which the detection step relates is greater than the amount of organisms initially contained in the sample, preferably greater than twice this amount, preferably greater than 10 times this amount, preferably greater than 100 times, preferably greater than 1,000 times, preferably greater than 10,000 times, and sometimes preferably greater than 100,000 times, or even than 1,000,000 times, this initial amount.

Detection

The purpose of the detection carried out in step (c) is to identify whether the sought organisms are present or not; or else to count them (or to determine their concentration in the investigated sample), or else to characterize their nature or their type.

The detection is based on the measurement of a property. It is also possible to use a combination of several property measurements. Each measurement may be of a direct or indirect nature.

The property measurement may be carried out in situ, on the particle bed located in the capture area or else ex situ, i.e. out of the capture area.

The in situ measurement has the advantage of simplicity and of compactness. The ex situ measurement may allow a larger analysis field, and notably allow typing of the captured organisms.

According to an embodiment of the ex situ alternative, the particles or part of the particles contained in the capture area (to which the organisms to be detected are possibly bound) are withdrawn from the capture area (for example by increasing the fluid flow rate so as to overcome the force opposed to the flow, or by suppressing the force opposed to the flow) and transferred to another area of the device, before the detection step (c).

According to another embodiment of the ex situ alternative, the organisms possibly bound to the particles in the capture area are totally or partly released from the particles (for example, by circulating in the capture area a medium altering the interaction between the organisms and the particles), withdrawn from the capture area and transferred to another area of the device before the detection step (c).

According to another embodiment of the ex situ alternative, species secreted by the organisms possibly bound to the particles in the capture area or constituents of these organisms are withdrawn from the capture area and transferred to another area of the device before the detection step (c). In this embodiment, a preliminary step of cell lysis and more particularly proteolysis may notably be provided.

By "secreted species" is meant any type of molecular, multimolecular, organic or cellular species produced by the organisms present in the bed, naturally or subsequently to particular stimuli, apoptosis or lysis. These may for example be excreted proteins or peptides, signaling factors, exosomes, metabolites, nucleic acids, or any types of molecular aggregates, lysis products, but also organisms (for example cells) derived from the division or the modification of the organisms present in the bed.

Preferably, the detection of step (c) is carried out on at least 20% of the organisms present in the capture are at the end of step (b), more particularly preferably at least 50%, and even more preferably at least 80%.

The measured property may for example be a mechanical, hydrodynamic, dimensional property that may correspond to a measurement of a force, a displacement, a pressure, a flow rate, a mass or a density.

This may also be an optical property, such as an optical density, a turbidity, an optical radiation intensity at one or several wavelengths or in a range of wavelengths, an absorption coefficient radiation at one or more wavelengths or in a range of wavelengths.

The measured property is, for example, the volume occupied by the particles (and the bound organisms) in the capture area. It was observed that the volume occupied by the particles increases during the growth step because of this growth of the organisms. This increase in volume may be measured either directly or by means of a change of surface or length of the particle bed according to one or several directions.

In particular, measuring the time required for the volume occupied by the particles to reach a predetermined threshold value makes it possible to infer the concentration of organisms present in the capture area at the beginning of step (b) and therefore infer the concentration of organisms in the sample.

The measured property may further be a hydrodynamic property, such as a porosity, a viscosity, an elasticity or a viscoelasticity.

The measured property may further be a texture property, such as a granulosity, or any property affecting the visual aspect of an image of the particle bed (or of the sample fraction of the particles), or a function which may be derived from this image.

The measured property may further be an optical property; it is thus possible to proceed with a measurement of light intensity, of absorption, of fluorescence or of luminescence.

Step (c) may also implement a biological or biochemical detection, such as a genetic analysis, a proteomic analysis or the measurement of a metabolic activity.

In particular, a measurement of the ELISA type (immunoadsorption dosage by a bound enzyme), immunoagglutination, measurement of the concentration of chemical species or metabolites, DNA or RNA sequencing or genotyping, PCR, hybridization on hybridization networks or DNA chips or protein chips, or any other method involving a step of DNA amplification or hybridization.

When the measurement is carried out in situ in the capture area, direct measurements of a physical property, or of a texture property, or of an optical property, or a combination thereof, are preferred.

It may be advantageous to conduct the measurement in situ on a non-fluidized (compact) particle bed, for example when the measurements deals with the volume of the bed, but also for some biochemical measurements such as an immunoadsorption assay by a bound enzyme.

In the case of the ex situ measurement, it may for example be conducted along an outlet channel connected to the outlet of the capture area. Preferably, this outlet channel is not connected to the inlet of the capture area, which simplifies the handling of the fluids.

The detection may include or be preceded with a molecular amplification step. By "molecular amplification" is meant a method by which a multiplicity of molecules to be detected are obtained from a target molecule.

Molecular amplification may notably be an amplification of nucleic acids, and more particularly PCR (polymerization chain reaction).

Other examples of amplification of nucleic acids are reverse transcription (RT), isothermal, amplification of DNA, circular replication (RCA for "rolling circular amplification"), branched circular replication, circle to circle amplification (C2CA), DNA amplification facilitated by a loop (LAMP for "loop-mediated amplification"), NASBA amplification (for "nucleic acid sequence-based amplification"), TMA amplification (for "transcription-mediated amplification"), SMART (for "signal-mediated amplification of RNA technology"), HDA amplification (for "helicase-dependent amplification"), RPA amplification (for "recombinase polymerase amplification"), (CPA) amplification (for "cross-priming amplification"), SMART-AMP (for "Smart amplification"), RAM amplification (for "ramification amplification"), SDA amplification (for "strand displacement amplification"), NEAR amplification (for "nicking enzyme amplification reaction"), NEMA amplification (for "nicking enzyme amplification reaction"), ICA amplification (for "isothermal chain amplification"), EX-PAR amplification (for "exponential amplification reaction"), BAD amplification (for "beacon-assisted detection amplification") and amplification using the Phi29 DNA polymerase enzyme. Reference may be made to the article by Niemz et al. in *Trends in Biotechnology*, 29. 240-250 (2011) on this topic.

Molecular amplification may also be an enzymatic amplification. In this case, an enzyme is used which specifically (directly or indirectly) binds to a target molecule and which may transform a multiplicity of molecules of a substrate, wherein this transformation may be more easily detected than the initial target molecule. An example of enzymatic amplification is the ELISA technique.

Molecular amplification may also be a PLA amplification (for "proximity ligation assay") or be based on multiple and/or multiplexed hybridization. Kits for implementing such techniques are available commercially under the brands QuantiGene® or NanoString®.

Molecular amplification may also be of the catalytic type.

Molecular amplification may also be a chemiluminescence, electrochemiluminescence or electrochemistry technique.

The method of the invention may allow the typing of the organisms of the sample.

This typing can in particular be a cell typing.

Cell typing may consist in determining the particular strain of the organisms (for example of bacteria), or determining a class, a group, a species, a variety of these organisms, or any other characteristic of the classification of the species.

Cell typing may also make it possible to detect an abnormality of some cells among others, for example for pluricellular organism cells.

Typing may also consist in determining one or several properties of interest of genetically modified organisms.

Typing may also be genotyping. It may consist in determining the genotype of pathogenic organisms, cancer cells, fetal cells. It may consist in identifying on/off mutations or genome modifications on a large-scale, such as deletions, amplifications, rearrangements or insertions.

Typing may also be phenotyping. It may consist in determining the morphology, the structure, the proteome or the transcriptome of the organisms, or determining modifications of nucleic acids such as methylations, phosphorylations or other modifications of intracellular nucleic acids.

Typing may also be functional typing. It may consist in evaluating the production of some proteins, metabolites or nucleic acids such as microRNAs, the metabolization of some species, or the resistance to some species, like in particular the resistance to toxic agents or drugs. Functional typing may also involve the evaluation of a proliferation capability, or a differentiation capability, a pluripotent character.

In order to allow the implementation of step (c) of the method, the fluidic system of the invention includes adequate means, and in particular a system for measuring at least one physical, chemical or biological property.

This measurement system may be associated with the chamber including the capture area (for an in situ measurement) or be associated with another chamber of the fluidic system (for an ex situ measurement), which may be described as a detection chamber.

The measurement system may include a device for imaging the contents of the fluidic system and notably of the detection chamber or of the capture area. This imaging device is preferably associated with image analysis software.

The measurement system may include one or several light sources, and one or several light intensity detectors. It may include a spectrometer, a frequency analyzer, an impedance analyzer or a conductimeter (with electrodes).

The measurement system may include means for measuring hydrodynamic resistance, viscosity, permeability, pressure or flow rate.

The measurement system may further include a device for measuring a biological property, like a sequencer, an electrophoresis device, a mass spectrometer, a PCR apparatus, a plasmon resonance system, a quartz microscale or a fluorimeter.

The measurement which is carried out makes it possible to infer information relating to the presence, the dead or live condition, the concentration or the type of the organisms of the sample.

The inference of this information may be carried out by means of a computer program, or optionally by means of an abacus or a mathematical formula.

Analytical Applications

The invention makes it possible to carry out at least one operation of identification, detection, analysis, identification, genotyping, quantification or phenotyping of organisms present in a sample.

The invention may make it possible to determine whether a sample contains live organisms (as opposed to dead organisms).

The invention may also make it possible to count the organisms (or determine the concentration of organisms in the sample).

The invention may also make it possible to determine the type of organisms possibly present in the sample.

The invention may also make it possible to determine the capabilities of development, of proliferation or of division of the organisms.

The invention is particularly of interest for the detection of organisms selected from among bacteria, unicellular or pluricellular parasites, fungi, mammal cells and plant cells.

According to particular embodiments, the organisms at stake are pathogenic organisms; or are stem cells; or are cancer cells.

The invention is notably applicable in the detection of the effect of molecules and notably of drugs on cells or other organisms. To this end, it is possible to provide a circulation step in the capture area of a fluid containing a molecule or an investigated drug, after step (a), and notably: either between step (a) and step (b); or during step (b); or after step (b).

The invention may be applied for implementing a diagnostic analysis (in human or veterinary medicine).

The invention may be applied for implementing an environmental analysis, such as the research for or identification of organisms (notably bacteria, or pathogenic organisms) in water or in the soil for example.

The invention may be applied for implementing an analysis of bacteria present in animals and notably in mammals (bacteriome of the digestive tract, bacteriome of the skin, etc.).

The invention may be applied for identifying or selecting genetically modified organisms. The invention may make it possible to genotype or phenotype organisms (and notably pathogenic organisms).

The sample used in the method of the invention may be a sample of a bodily fluid such as blood, saliva, cerebrospinal liquid, amniotic liquid, urine, lymph, a biopsy puncture, stools or a sample derived from one of these bodily fluids.

The invention may notably be applied to the diagnostic of a urinary infection; it may also be applied to the diagnostic of a septicemia.

The invention may also be applied to the detection of an infection by a pathogen, for example, detection of an infection by *E. coli, Salmonella, C. difficile, Streptococcus*, or the agent of SARS.

Alternatively, the sample may also derive from a foodstuff, or may be sampled in the environment.

By way of example, the method of the invention may be applied to the detection of the presence of the following organisms in foodstuffs, and notably in dairy products (such as powdered milk, cheese, butter, ice cream, etc.):

salmonellas (detection of the presence or absence of at least one salmonella in 25 g of product);

Enterobacteriaceae (notably detection of a concentration greater than or equal to 1 or 5 cfu per mL, or detection of the presence or absence of at least one unit in 10 g of product);

*E. coli* (notably detection of a concentration greater than or equal to 10 or $10^2$ or $10^3$ cfu per g);

staphylococci with positive coagulase (notably detection of a concentration greater than or equal to 10 or $10^2$ or $10^3$ or $10^4$ or $10^5$ cfu per g); *Bacillus cereus* (notably detection of a concentration greater than or equal to 1 cfu per mL, or to 50 or 500 cfu per g);

aerobic flora (notably detection of a concentration greater than or equal to 1 cfu per mL);

sulfite reducing bacteria (notably detection of a concentration greater than or equal to 1 cfu per mL);

*Listeria monocytogenes* (notably detection of a concentration greater than or equal to 1 unit in 25 g of product).

Preparatory Applications

The invention may also be applied to the preparation or the micro-preparation of organisms. Actually, it makes it possible to capture a very small number of organisms, to multiply and optionally characterize them, in a compact and highly automated device.

Thus, a method for preparing organisms according to the invention is implemented in the same way as any of the detection methods described above, except that:

the liquid sample contains parent organisms capable of binding to the particles of the capture area;

a collection step is provided, at the outlet of the capture area, for organisms derived from the division of the parent organisms.

In such a preparation method, the step of determining the presence, nature or concentration of the organisms in the capture area, or the step of measuring a physical property of the capture area, are optional.

However, advantageously, at least one of these steps is actually present, in which case the method of the invention is both a method for detecting organisms in a liquid sample and for preparing organisms from this liquid sample.

Advantageously, the method for preparing organisms according to the invention is implemented in a fluidic system according to the invention.

Such a fluidic system thus includes collection means, at the outlet of the capture area, for organisms derived from the division of the parent organisms. It may or may not include means for measuring a physical property of the capture area and/or means for determining the presence or concentration or nature of the organisms in the sample described above in connection with the fluidic systems dedicated to detection.

In particular, the preparatory method may be of interest in biotechnology, for selecting and preparing organisms having interesting features for a particular application.

It may also be of interest for selecting and producing progenitor cells, stem cells, hematopoietic cells, hematopoietic stem cells, or endothelial colony forming cells.

It may for example have applications for the capture and multiplication, from blood samples of a patient, of endothelial colony forming cells, for regenerative medicine applications, or for the capture and multiplication of primary or induced stem cells.

The invention is of particular interest in these applications owing to the capability, demonstrated in example 5 below, of capturing cells according to specific criteria and then continuously releasing species produced by these cells, and notably other cells, either identical or different, derived from the cells captured in a first phase.

EXAMPLES

The following examples illustrate the invention without limiting it.

Example 1—Estimation of the Capture Rate

A microfluidic system according to FIG. 1 is made. The chamber 2 has a length of 21 mm and a thickness of 50 μm, with a width varying from 100 μm to 2 mm (maximum width area).

The microfluidic system is prepared in polydimethylsiloxane according to the microlithography procedure described in the article by Mohamadi et al. in *Biomicrofluidics*, 5,044114 (2011).

For the generation of the magnetic field, a permanent magnet is used of the NdFeB1 type, placed in proximity to the chamber 2: the distance between the magnet and the microfluidic system is 2 mm. The magnet is magnetized in its largest dimension and has a permanent magnetic field of 1.47 T. It has a size of 30×20×20 mm.

The system is similar to the one in Examples 1, 2, 3, 4 and 5 of document WO 2014/037674, to which reference is expressly made for more details.

In the present example, the purpose is the capture of salmonellas.

The particles used are anti-salmonella Dynabeads® (marketed by Life Technologies®), in a total amount of 50 μg.

The investigated organisms are salmonellas (species *Salmonella typhimurium*). The samples containing salmonellas are produced by dilution of the bacteria in a phosphate salt buffer with addition of 0.1% of bovine serum albumin (BSA) from colonies grown on Petri dishes.

In order to carry out the capture of the bacteria by the particle bed, a sample is injected through the capture area with a flow rate of 1,000 nL/min. This step lasts for 50 minutes, for a sample of 50 μL (containing 400 bacteria).

Then washing is carried out with a phosphate salt buffer with 0.1% of BSA. The flow rate is adjusted to 1,500 nL/min, and the injected liquid volume is 40 μL.

A first estimation of the capture rate of bacteria is achieved by measuring the bacterial content in liquids recovered at the outlet of the system (90 μL corresponding to the passing of the sample and of the washing buffer). The measurement is conducted by culturing on a Petri dish and counting the formed colonies.

A second estimation is achieved by removing the particles of the microfluidic system, and by culturing the captured bacteria.

Both estimations are consistent for providing a capture rate of about 90%.

Further, the specificity of the capture of the bacteria was already illustrated notably in Example 5 of document WO 2014/037674.

Example 2—Growth In Situ of the Bacteria and Viewing with Fluorescence

In this example, fluorescent salmonellas are used (marked with the green fluorescent protein or GFP).

The same procedure is resumed as in example 1, but after the step of capturing the bacteria, a nutritive medium is passed into the capture area (LB medium for "lysogeny broth"). The flow rate is adjusted to 150 nL/min.

Self-regulating heating is used, by means of a system consisting of a glass side covered with an indium-tin oxide layer, with a thermocouple and a power supply controlled by a PID-type regulation. A current circulates in two copper electrodes adhered to the oxide layer and connected to the power supply system, which induces a heating of the plate by Joule effect. The temperature is adjusted to the set value of 37° C.

During the culture phase, at regular intervals, the power supply is cut off in the growth medium, in order to switch from the fluidized bed state to the compact bed one, and then one back to the fluidized mode after the measurement.

This makes it possible to measure the average intensity of the fluorescence of the compact particle bed at regular intervals, by acquiring images taken with a microscope.

FIG. 4 shows the change in fluorescence over time. It expresses a strong increase in the number of bacteria during the growth step.

Example 3—Growth In Situ of the Bacteria and Viewing by Optical Imaging

The same procedure is resumed as in example 2, but without conducting any fluorescence measurement.

Using a camera, images of the bed are taken (in the compact mode). Gradually during the division of the bacteria, it is possible to view the global volume of the bed in a compact mode, or the advance of the front of the bed (i.e. the longitudinal dimension of the bed in the chamber comprising the capture area).

The image J software is used to for measuring the advance of the front of the bed in the compact mode over time.

It can be seen that during a first phase, the size of the bed of particles does not change. Next, the size of the bed starts to rapidly increase, which is expressed by an advance of the measured front. If the growth of the bacteria is of the exponential type, the advance movement of the front is approximately linear, given that the width of the chamber increases along its axis.

By using several initial concentrations of salmonellas in the sample, it can be seen that the expansion of the volume of the bed of particles has a similar profile but that the starting time of the expansion of the bed varies. It is therefore possible to infer the initial concentration of bacteria from the starting time of expansion of the bed, or by determining the time at the end of which this concentration reaches a certain threshold. For example, for a simple model of exponential growth, the time required for the expansion of the bed, t, follows a logarithmic law as a function of the initial number of bacteria N, of the form $t=-a \ln(N)+b$.

Figure 5:
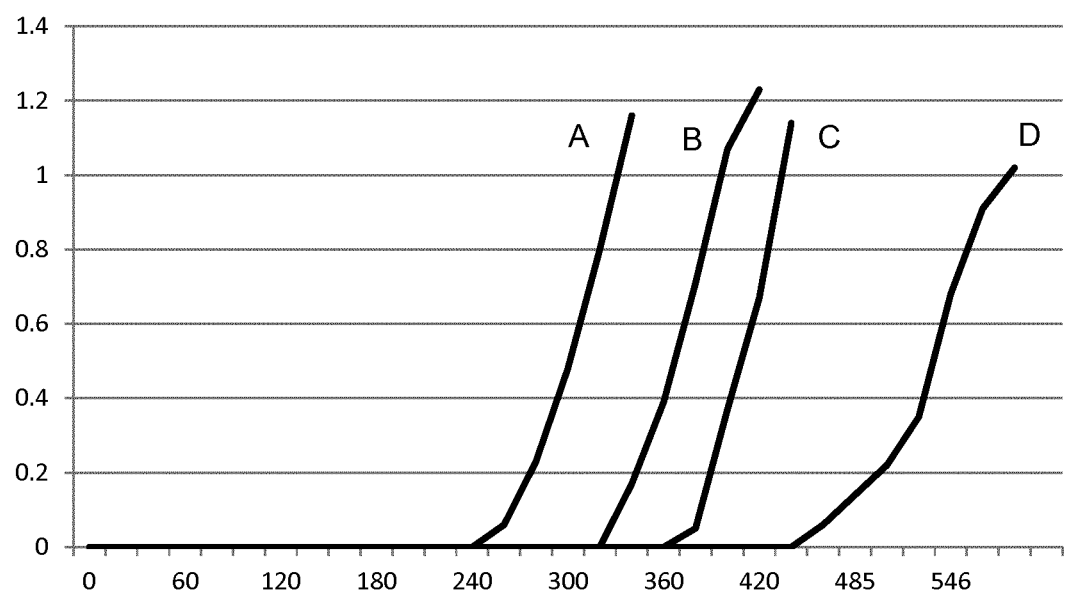
FIG. 5 is a graph showing the advance of the front of particle bed having captured bacteria (on the Y-axis, in mm) according to the incubation period of the particles with a growth medium, in a microfluidic system of the invention, (on the X-axis, in minutes). The different curves correspond to different initial concentrations of bacteria in the initial sample. Reference will be made to example 3 for more details.

Thus, with reference to FIG. 5, the progression of the front of the bed of particles in the channel is compared for a sample of 50 μL containing either 400 bacteria (curve A), or 100 bacteria (curve B), or 30 bacteria (curve C), or 5 bacteria (curve D). From these curves, it is possible to infer under these experimental conditions the parameters $a=45$ and $b=510$.

Example 4—Method Including a DNA Molecular Amplification Step by PCR, after the Growth Step After capturing the bacteria on the magnetic particles as described above, the latter are lysed by injection within the bed of magnetic particles of a solution (10 μL) allowing the lysis and release of DNA and which is directly compatible with an amplification by qPCR (lysis and Go PCR reagent, Thermo). In order to improve the performances of the bacterial lysis and deactivate the exonucleases, the whole system undergoes the temperature cycle shown in the table below. The solution recovered after this lysis step is directly mixed with a commercial mixture (or mix) for PCR (for example iQ-Check Salmonella II Kit) and is thus effective for the amplification of genomic or plasmid DNA. To this end, the lysate is placed in a thermocycler in order to carry out the PCR, by adding the primers into the tube, and the PCR mix in a lysate/mix ratio (1:10, v/v). The presence of salmonellas in the initial samples is checked by comparing the "Ct" provided by the analysis software of the PCR results: a Ct of less than 30 is selected as an indicator of a presence of salmonellas.

| Cycle | Temperature (° C.) | Time (seconds) |
|---|---|---|
| 1 | 65 | 30 |
| 2 | 8 | 30 |
| 3 | 65 | 90 |
| 4 | 97 | 180 |
| 5 | 8 | 60 |
| 6 | 65 | 180 |
| 7 | 97 | 60 |
| 8 | 65 | 60 |
| 9 | 80 | maintenance |

Example 5—Method Including a Step of Releasing Organisms Produced in the Fluidized Bed After capturing the bacteria on the magnetic particles as described above, the leaving liquid exiting the fluidized bed is collected over time in the form of aliquots of 10 µl, at a rate of one aliquot per hour. The amount of bacteria contained in each of these aliquots is then measured in a conventional manner by spreading out on culture plates. The table below provides the number of released bacteria over time, from an initial amount of 500 bacteria in 50 µL, i.e. an initial concentration of 100 bacteria in 10 µL.

| Duration (hours) | Number of bacteria in 10 µL |
|---|---|
| 1 | 3 |
| 2 | 3 |
| 3 | 6 |
| 4 | 50 |
| 5 | 512 |
| 6 | 8488 |

This experiment shows, on the one hand, the great capture efficiency of the invention, since at the beginning only 3 bacteria are released in 10 µL (versus 100 at the inlet of the device), and also the capability of the invention of continuously and efficiently producing a large number of bacteria, at a concentration much higher than the concentration of the initial sample.

The invention claimed is:

1. A method for detecting organisms in a liquid sample, the method comprising the steps:
   (a) providing particles in a liquid medium and subjecting said particles to a hydrodynamic flow, in a capture area, wherein the organisms to be detected are capable of binding to these particles;
   (b) circulating the sample through the capture area;
   (c) measuring a physical property of the capture area, during and/or after circulating the sample, so as to deduce therefrom the presence or the concentration or the nature of the organisms in the sample; and
   (d) retaining the particles in the capture area between the inlet and the outlet of the hydrodynamic flow in the form of a fluidized bed when the capture area is subject to a hydrodynamic flow, in which the particles suspended in the flowing liquid medium behave like a fluid, are in motion relative to each another, and may adapt their mutual configuration to the shape of a chamber in which they are contained, but are not globally driven by said liquid medium, during at least part of the steps of circulating the sample and/or measuring a physical property.

2. The method according to claim 1, wherein the velocity of the hydrodynamic flow decreases in the capture area in the direction of the hydrodynamic flow.

3. The method according to claim 1, wherein the retention of the particles in the capture area is obtained by applying a force opposed to the hydrodynamic flow and wherein the force opposed to the hydrodynamic flow decreases in the capture area, in the direction of the hydrodynamic flow.

4. The method according to claim 3, wherein the force opposed to the hydrodynamic flow is a magnetic force, and the particles are magnetic particles.

5. The method according to claim 1 for screening drugs or biocides, further comprising a step of circulating a medium comprising a potential drug or biocide through the capture area.

6. The method according to claim 1, wherein the physical property is a force, a displacement, a pressure, a flow rate, a mass, a density, a porosity, a viscosity, an elasticity, a viscoelasticity, an optical density, a turbidity, a texture property, an intensity measurement or a radiation absorption coefficient.

7. The method according to claim 1, wherein the physical property is a volume occupied by the particles in the capture area or a dimension of this occupied volume.

8. The method according to claim 1, further comprising the step of circulating a growth medium comprising nutrients for the organisms, through the capture area, after the step of circulating the sample through the capture area.

9. The method according to claim 8, wherein the particles are retained in the capture area as a fluidized bed during at least part of the step of circulating the growth medium through the capture area.

10. The method according to claim 8, wherein the particles are retained in the capture area as a fluidized bed during the totality of the step of circulating the growth medium through the capture area.

11. The method according to claim 8, wherein the step of measuring the physical property of the capture area is carried out during the step of circulating the growth medium through the capture area.

12. The method according to claim 8, wherein the step of measuring the physical property of the capture area is carried out after the step of circulating the growth medium through the capture area.

13. The method according to claim 1, wherein the organisms are selected from the group consisting of prokaryotic cells, bacteria, yeasts, unicellular or pluricellular parasites, fungal cells, eukaryotic cells, mammal cells, plant cells, pathogenic organisms, stem cells, genetically modified organisms, cancer cells, endothelial cells, hematopoietic cells, epithelial cells, fetal cells, pluripotent cells, totipotent cells, induced pluripotent stem cells and functional assemblies of the above cells.

14. The method according to claim 1, wherein the particles have an average size Dv50 from 1 µm to 50 µm.

15. The method according to claim 1, wherein the particles are retained in the capture area as a fluidized bed during at least part of the step of circulating the sample through the capture area.

16. The method according to claim 1, wherein the particles are retained in the capture area as a fluidized bed during the totality of the step of circulating the sample through the capture area.

17. The method according to claim 1, wherein the particles are retained in the capture area as a fluidized bed during at least part of the step of measuring the physical property of the capture area.

18. The method according to claim 1, wherein the particles are retained in the capture area as a compact bed during at least part of the step of measuring the physical property of the capture area.

\* \* \* \* \*